(12) United States Patent
Patwardhan et al.

(10) Patent No.: US 9,861,337 B2
(45) Date of Patent: Jan. 9, 2018

(54) APPARATUS AND METHOD FOR DETECTING CATHETER IN THREE-DIMENSIONAL ULTRASOUND IMAGES

(71) Applicant: General Electric Company, Schenectady, NY (US)

(72) Inventors: Kedar Anil Patwardhan, Latham, NY (US); David Martin Mills, Niskayuna, NY (US); Gang Liu, Wuxi (CN); Kunlin Cao, Niskayuna, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 972 days.

(21) Appl. No.: 14/172,087

(22) Filed: Feb. 4, 2014

(65) Prior Publication Data

US 2014/0221821 A1 Aug. 7, 2014

(30) Foreign Application Priority Data

Feb. 4, 2013 (CN) .......................... 2013 1 0044619

(51) Int. Cl.
*G06K 9/00* (2006.01)
*A61B 8/08* (2006.01)

(52) U.S. Cl.
CPC ............ *A61B 8/0841* (2013.01); *A61B 8/483* (2013.01); *A61B 8/5223* (2013.01); *A61B 8/5207* (2013.01)

(58) Field of Classification Search
CPC ..... A61B 8/0841; A61B 8/483; A61B 8/5207; A61B 8/5223
See application file for complete search history.

(56) References Cited

U.S. PATENT DOCUMENTS

| | | | |
|---|---|---|---|
| 5,349,524 A | 9/1994 | Daft et al. |
| 5,429,137 A | 7/1995 | Phelps et al. |
| 5,560,363 A | 10/1996 | Torp et al. |
| 5,720,285 A | 2/1998 | Petersen |
| 5,957,846 A | 9/1999 | Chiang et al. |
| 6,246,898 B1 | 6/2001 | Vesely et al. |
| 6,251,072 B1 | 6/2001 | Ladak et al. |
| 6,336,899 B1 | 1/2002 | Yamazaki |
| 6,385,332 B1 | 5/2002 | Zahalka et al. |

(Continued)

FOREIGN PATENT DOCUMENTS

| | | |
|---|---|---|
| CN | 101393644 A | 3/2009 |
| CN | 101889878 A | 11/2010 |

(Continued)

OTHER PUBLICATIONS

Unofficial translation of Chinese Office Action and Search Report issued in connection with corresponding CN Application No. 201310044619.8 dated Jan. 5, 2016.

(Continued)

*Primary Examiner* — Tom Y Lu

(57) ABSTRACT

An apparatus for detecting catheter(s) in 3D ultrasound images includes a 3D ultrasound image acquiring module and a catheter centerline 3D trajectory generating module. The 3D ultrasound image acquiring module is used for capturing an original 3D ultrasound image. The catheter centerline 3D trajectory generating module is used for detecting and visualizing a catheter in the 3D ultrasound image.

18 Claims, 22 Drawing Sheets

(56) References Cited

U.S. PATENT DOCUMENTS

| | | |
|---|---|---|
| 6,419,632 B1 | 7/2002 | Shiki et al. |
| 6,464,641 B1 | 10/2002 | Pan et al. |
| 6,728,566 B1 | 4/2004 | Subramanyan et al. |
| 6,782,284 B1 | 8/2004 | Subramanyan et al. |
| 7,043,290 B2 | 5/2006 | Young et al. |
| 7,397,935 B2 | 7/2008 | Kimmel et al. |
| 7,494,469 B2 | 2/2009 | Bruestle |
| 7,558,618 B1 | 7/2009 | Williams |
| 7,666,143 B2 | 2/2010 | Wilser et al. |
| 8,200,313 B1 | 6/2012 | Rambod et al. |
| 2002/0118869 A1 | 8/2002 | Knoplioch et al. |
| 2003/0060700 A1 | 3/2003 | Solf et al. |
| 2003/0125624 A1 | 7/2003 | Shiki |
| 2004/0097806 A1 | 5/2004 | Hunter et al. |
| 2004/0249270 A1* | 12/2004 | Kondo ............... G06T 15/08 600/425 |
| 2005/0015006 A1 | 1/2005 | Mitschke et al. |
| 2005/0249399 A1 | 11/2005 | Tek et al. |
| 2006/0036167 A1* | 2/2006 | Shina ................. A61B 6/12 600/433 |
| 2006/0064006 A1* | 3/2006 | Strommer ............ A61B 5/06 600/415 |
| 2006/0079782 A1 | 4/2006 | Beach et al. |
| 2006/0251304 A1 | 11/2006 | Florin et al. |
| 2007/0081712 A1 | 4/2007 | Huang et al. |
| 2007/0167801 A1 | 7/2007 | Webler et al. |
| 2008/0015440 A1 | 1/2008 | Shandas et al. |
| 2008/0091171 A1 | 4/2008 | Strommer et al. |
| 2008/0119736 A1 | 5/2008 | Dentinger |
| 2008/0137926 A1 | 6/2008 | Skinner et al. |
| 2009/0306507 A1 | 12/2009 | Hyun et al. |
| 2010/0063398 A1 | 3/2010 | Halmann et al. |
| 2010/0104168 A1 | 4/2010 | Dobbe |
| 2010/0191101 A1 | 7/2010 | Lichtenstein |
| 2011/0150274 A1* | 6/2011 | Patwardhan .......... G06T 7/0012 382/103 |
| 2011/0166451 A1 | 7/2011 | Blaivas et al. |

FOREIGN PATENT DOCUMENTS

| | | |
|---|---|---|
| CN | 101953696 A | 1/2011 |
| EP | 1152372 A2 | 11/2001 |
| JP | 2000126181 A | 5/2000 |
| JP | 2002092621 A | 3/2002 |
| JP | 2004201873 A | 7/2004 |
| JP | 2005510280 A | 4/2005 |
| JP | 2005510327 A | 4/2005 |
| JP | 2005165791 A | 6/2005 |
| JP | 2006068351 A | 3/2006 |
| JP | 2009131406 A | 6/2009 |
| WO | 2004052016 A2 | 6/2004 |

OTHER PUBLICATIONS

Duda et al., "Use of the Hough Transformation to Detect Lines and Curves in Pictures", Communications of the ACM, vol. 15, No. 1, pp. 11-15, 1972.

Viola et al.,"Robust Real-Time Object Detection", International Journal of Computer Vision, Cambridge Research Lab, Feb. 2001, 23 pages.

Slabaugh et al., "Statistical Region-Based Segmentation of Ultrasound Images", Ultrasound in Medicine and Biology, vol. 35, No. 5, pp. 781-795, 2009.

Unofficial English translation of Chinese Office Action and Search Report issued from corresponding CN Application No. 201310044619.8 dated May 26, 2015.

Wang et al., "An Evaluation of Using Real-Time Volumetric Display of 3D Ultrasound Data for Intracardiac Catheter Manipulation Tasks", Volume Graphics 2005 Fourth International Workshop on, pp. 41-45, Jun. 2005.

Okazawa et al., "Methods for Segmenting Curved Needles in Ultrasound Images", Medical Image Analysis, pp. 330-342, vol. 10, 2006.

Barva et al., "Parallel Integral Projection Transform for Straight Electrode Localization in 3D ultrasound Images", IEEE Transactions on Ultrasounics Ferroelectrics and Frequency control, vol. 55, issue 7, 2008.

Uhercik et al., "Multi-Resolution Parallel Integral Projection for Fast Localization of a Straight Electrode in 3D Ultrasound Images", ISBI, 2008.

Neshat et al. "Real-Time Parametric Curved Needle Segmentation in 3D Ultrasound Images", Biomedical Robotics and Biomechatronics, 2008 Biorob 2008 2nd IEEE RAS & EMBS International Conference on, pp. 670-675, Oct. 2008.

Aboofazeli et al., "A New Scheme for Curved Needle Segmentation in Three-Dimensional Ultrasound Images", ISBI, pp. 1067-1070, 2009.

Clendenen et al., "Real-Time 3-Dimensional Ultrasound-Assisted Infraclavicular Brachial Plexus Catheter Placement: Implications of a New Technology", Anesthesiology Research and Practice, pp. 1-4, vol. 2010, 2010.

"Sidney Health Center Upgrades to a 4D Ultrasound System", Sidney Health Center, May 22, 2012.

M. Barva, J. Kybic, J-M. Mari, C. Cachard, and V. Hlavac: "Automatic Localization of Curvilinear Object in 3D Ultrasound Images". SPIE 2005.

Skolnik, "Introduction to Radar Systems", Second Edition, pp. 392-395, 1980.

Kasai et al., "Real-time two-dimensional blood flow imaging using an autocorrelation technique", IEEE Transactions on Sonics and Ultrasonics, vol. No. SU-32, Issue No. 3, pp. 458-464, May 1985.

Oppenheim et al., "Discrete-Time Signal Processing", Prentice Hall: Englewood Cliffs, pp. 402-407, 1989.

Papoulis, Probability, Random Variables, and Stochastic Processes, Third Edition, pp. 78-79, 138-141 & 264-275, 1991.

Gonzalez et al., "Digital Image Processing", Addison-Wesley Publishing: Reading Massachusetts, pp. 40-43, 1992.

Jensen, "Estimation of Blood Velocities Using Ultrasound", Cambridge University Press, pp. 6-15 & 154-157, 1996.

Torp, "Clutter rejection filters in color flow imaging: a theoretical approach", IEEE Transactions on Ultrasonics, Ferroelectrics, and Frequency Control, vol. No. 44, Issue No. 2, pp. 417-424, Mar. 1997.

Chutatape et al., "Retinal Blood Vessel Detection and Tracking by Matched Gaussian and Kalman Filters", IEEE Engineering in Medicine and Biology Society, Proceedings of the 20th Annual International Conference of the IEEE, Piscataway, NJ, US, vol. No. 20, Issue No. 6, pp. 3144-3149, Oct. 29, 1998.

Cohen et al., "New Maximum Liikelihood Motion Estimation Schemes for Noisy Ultrasound Images", Pattern Recognition, vol. No. 35, Issue No. 2, pp. 455-463, Feb. 1, 2002.

Hernandez-Hoyos et al., "Computer-assisted Analysis of Three-dimensional MR Angiograms", vol. No. 22, Issue No. 2, pp. 421-436, Mar. 1, 2002.

Mansard et al., "Quantification of Multicontrast Vascular MR Images with NLSnake, an Active Contour Model: In Vitro Validation and In Vivo Evaluation", Magnetic Resonance in Medicine, vol. No. 51, Issue No. 2, pp. 370-379, Feb. 28, 2004.

Matsuyama et al., "Developing Man-Machine Symbiotic Systems", Journal of Japanese Society for Artificial Intelligence, vol. No. 19, Issue No. 2, pp. 257-266, Mar. 2004.

Noble et al., Ultrasound Image Segmentation: A Survey, IEEE Transactions on Medical Imaging, vol. No. 25, Issue No. 8, pp. 987-1010, Aug. 2006.

Guerrero et al., "Real-Time Vessel Segmentation and Tracking for Ultrasound Imaging Applications", IEEE Transactions on Medical Imaging, vol. No. 26, Issue No. 8, pp. 1079-1090, Aug. 2007.

Lee et al., "Automatic Segmentation of 3D Micro-CT Coronary Vascular Images", Medical Image Analysis, vol. No. 11, Issue No. 6, pp. 630-647, Oct. 27, 2007.

Nowinski et al., "A 3D Model of Human Cerebrovasculature Derived from 3T Magnetic Resonance Angiography", Neuroinform, Springer, vol. No. 7, Issue No. 1, pp. 23-36, Mar. 2009.

Lesage et al., "A Review of 3D Vessel Lumen Segmentation Techniques: Models, Features and Extraction—Schemes", Medical Image Analysis, vol. No. 13, Issue No. 6, pp. 819-845, Dec. 1, 2009.

(56) References Cited

OTHER PUBLICATIONS

Non-Final Rejection towards related U.S. Appl. No. 11/562,631 dated Dec. 10, 2010.
International Invitation to Pay Additional Fees issued in connection with related PCT Application No. PCT/US2010/059358 dated Apr. 29, 2011.
Non-Final Rejection towards related U.S. Appl. No. 12/208,090 dated May 26, 2011.
International Search Report and Written Opinion issued in connection with related PCT Application No. PCT/US2010/059358 dated Jun. 15, 2011.
Non-Final Rejection towards related U.S. Appl. No. 12/645,781 dated May 10, 2012.
Non-Final Rejection towards related U.S. Appl. No. 12/208,090 dated Jun. 7, 2012.
Notice of Allowance issued in connection with related U.S. Appl. No. 12/645,781 dated Mar. 15, 2013.
Office Action issued in connection with related CN Application No. 201080064647.0 dated Apr. 30, 2014.
Non-Final Rejection towards related U.S. Appl. No. 13/910,620 dated May 14, 2014.
Non-Final Rejection towards related U.S. Appl. No. 13/910,603 dated May 15, 2014.
Japanese Search Report issued in connection with related JP Application No. 2012-546000 dated Aug. 15, 2014.
Office Action issued in connection with related JP Application No. 2012-546000 dated Sep. 2, 2014.
Notice of Allowance issued in connection with related U.S. Appl. No. 13/910,620 dated Sep. 11, 2014.
Final Rejection towards related U.S. Appl. No. 13/910,603 dated Sep. 12, 2014.
Notice of Allowance issued in connection with related U.S. Appl. No. 13/910,620 dated Oct. 22, 2014.
Non-Final Rejection towards related U.S. Appl. No. 13/910,603 dated Dec. 29, 2014.
Notice of Allowance issued in connection with related U.S. Appl. No. 13/910,603 dated May 27, 2015.
Notice of Allowance issued in connection with related JP Application No. 2012-546000 dated Dec. 22, 2015.
U.S. Appl. No. 12/645,781, filed Dec. 23, 2009, Patwardhan et al.
U.S. Appl. No. 13/910,620, filed Jun. 5, 2013, Patwardhan et al.
U.S. Appl. No. 13/910,603, filed Jun. 5, 2013, Patwardhan et al.
U.S. Appl. No. 11/562,631, filed Nov. 22, 2006, Dentinger.
U.S. Appl. No. 12/208,090, filed Sep. 10, 2008, Halmann et al.

\* cited by examiner

APPARATUS AND METHOD FOR DETECTING CATHETER IN THREE-DIMENSIONAL ULTRASOUND IMAGES

TECHNICAL FIELD

The subject matter disclosed herein relates to an apparatus and method for medical imaging. More specifically, embodiments of the present invention relate to detecting a catheter in 3D ultrasound images.

BACKGROUND

Several medical procedures require placement of catheters/needles inside a biological tissue (such as blood vessel) of a human body. For example, FIG. 1 shows a schematic view of a peripherally inserted central catheter (PICC) operation 100. In the PICC operation 100, a catheter 110 is inserted into a blood vessel 120 from the arm to the chest. The tip 112 of the catheter 110 usually needs to be localized at a proper position, maybe nearby the heart 130. Typically, the placement of the catheter 110 is currently performed blindly and then confirmed by X-ray detection after completion of the PICC operation 100. X-ray imaging has adequate resolution to see tiny blood vessels, but also causes radiation-related complications.

Toward improved and safer care for patients, including fragile infants, ultrasound guided catheter percutaneous insertions have been widely adopted in clinical practice. Detecting the catheter in ultrasound images can guide clinicians to insert the catheter into a predetermined location of a biological tissue. However, ultrasound images suffer from heavy speckle noise and lower spatial resolution. It is challenging for a clinician to visualize and follow the moving blood vessels in the raw, real-time images when both hands are occupied, i.e., wherein one hand holds and sweeps the probe and the other handles the catheter delicately. According to clinical literature, improper positioning of the tip of the catheter is a suspected cause of severe complications that may lead to death of fragile patients.

BRIEF DESCRIPTION

An apparatus and a method for detecting a catheter in 3D ultrasound images are provided. In an embodiment, the apparatus includes a 3D ultrasound image acquiring module and a catheter centerline 3D trajectory generating module. The 3D ultrasound image acquiring module is used for capturing an original 3D ultrasound image. The catheter centerline 3D trajectory generating module is used for detecting and visualizing a catheter in the 3D ultrasound image.

In an embodiment, there is provided a method, comprising: capturing an original 3D ultrasound image; generating a first likelihood map of catheter location comprising a plurality of candidate catheters therein from the original 3D ultrasound image; detecting a true catheter from the plurality of candidate catheters; and displaying the true catheter on a display.

In another embodiment, there is provided a method, comprising: capturing an original 3D ultrasound image; calculating a 3D trajectory of a catheter centerline of a catheter; calculating a 3D trajectory of a blood vessel; creating a blood vessel centerline 2D cut image along a blood vessel centerline trajectory based on the calculated 3D trajectory of the blood vessel; and projecting the 3D trajectory of the catheter centerline of the catheter onto the created blood vessel centerline 2D cut image.

In yet another embodiment, there is provided a method, comprising: capturing an original 3D ultrasound image; calculating a 3D trajectory of a catheter; calculating a 3D trajectory of a blood vessel; determining which one of detection results of the catheter and the blood vessel is not satisfied based on predetermined criterion; when the detection result of the blood vessel is not satisfied compared with the detection result of the catheter, re-calculating a 3D trajectory of the blood vessel based on a ROI of the catheter; when the detection result of the catheter is not satisfied compared with the detection result of the blood vessel, re-calculating a 3D trajectory of a catheter centerline of the catheter based on a ROI of the blood vessel; and combining the calculated catheter image and the calculated blood vessel image to become a composite image.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

In the following detailed description, reference is made to the accompanying drawings that form a part hereof, and in which is shown, by way of illustration, specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Unless defined otherwise, technical and scientific terms used herein have the same meaning as is commonly understood by one of ordinary skill. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items, and terms such as "X-axis", "Y-axis", "Z-axis", "XY-axis", "YZ-axis", "XZ-axis", "front", "back", "bottom", and/or "top", unless otherwise noted, are merely used for convenience of description, and are not limited to any one position or spatial orientation. Moreover, the terms "coupled" and "connected" are not intended to distinguish between a direct or indirect coupling/connection between two components. Rather, such components may be directly or indirectly coupled/connected unless otherwise indicated.

Figure 1:
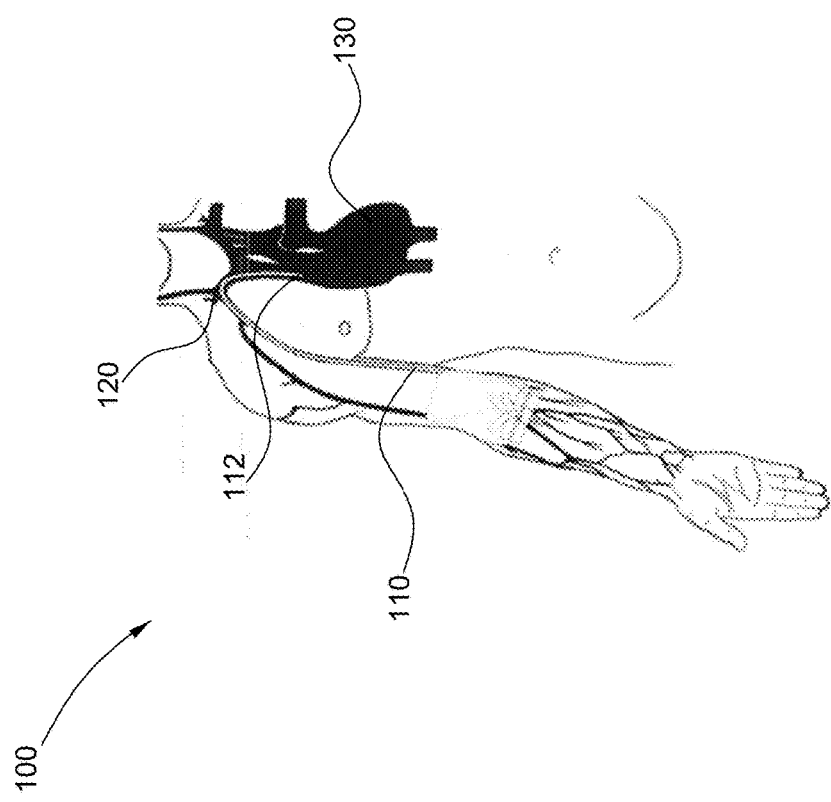
FIG. 1 is a schematic view of a peripherally inserted central catheter operation.
Figure 2:
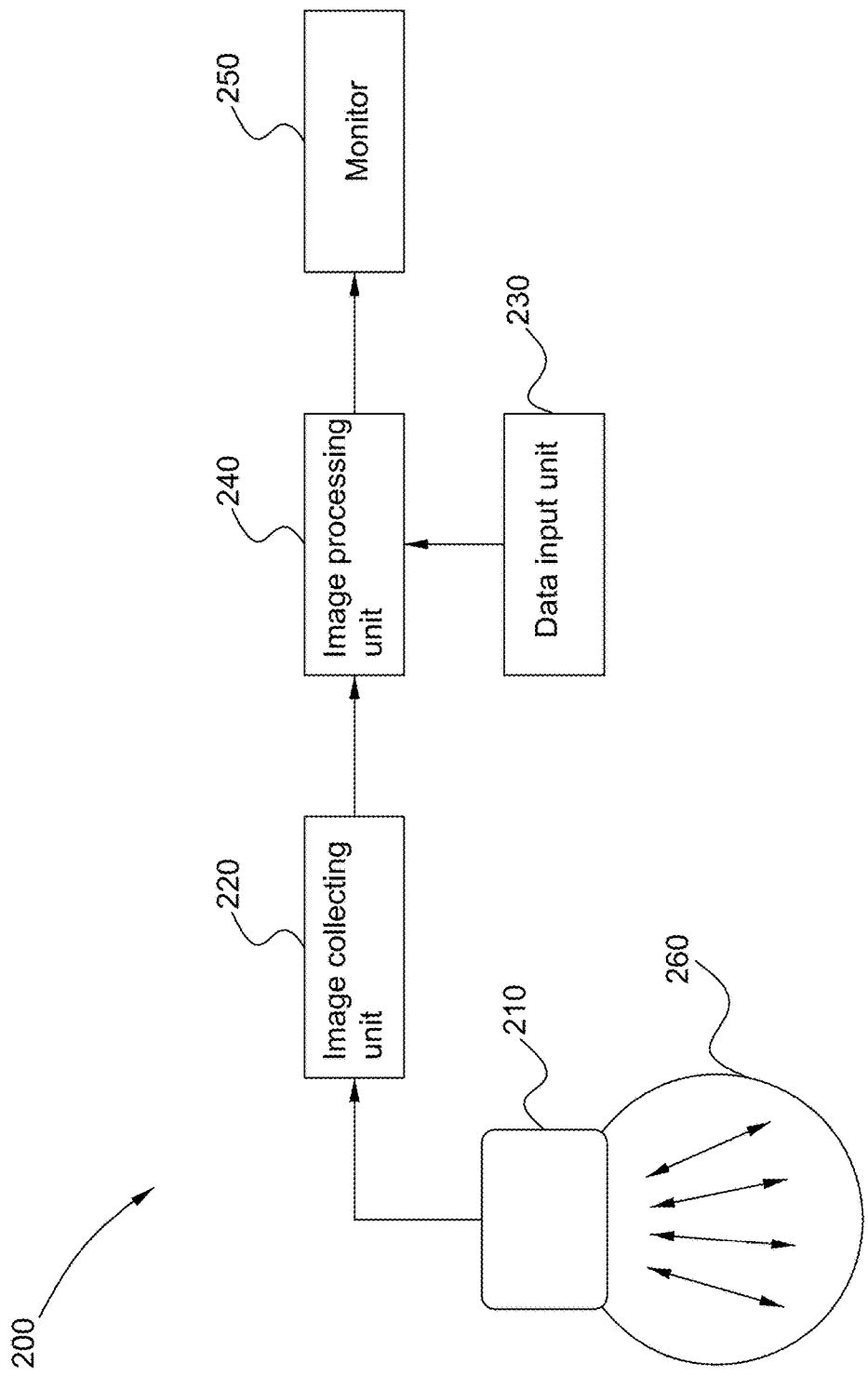
FIG. 2 is a schematic view of an apparatus for detecting catheters in 3D ultrasound images, according to one embodiment.

Referring to FIG. 2, a schematic view of an apparatus 200 for detecting a catheter in 3D ultrasound images, according to one embodiment is shown. The apparatus 200 is used to automatically detect/calculate 3D trajectory data (namely XYZ-axis coordinates in 3D space) of a catheter in captured 3D ultrasound images, such as during a PICC operation, which can easily and accurately guide clinicians to insert the catheter into a predetermined location of a blood vessel, or monitor the inserted catheter in real time for example. In one embodiment, the apparatus 200 may be used as either a stand-alone tool (such as a computer) communicated with an ultrasound device, or directly embedded in an ultrasound device. As used herein, the term "image" refers to multi-dimensional data composed of discrete image elements (e.g., pixels for 2D images and voxels for 3D images).

In the embodiment of FIG. 2, the apparatus 200 may include an ultrasound probe 210, an image collecting unit 220, a data input unit 230, an image processing unit 240, and a monitor 250. The ultrasound probe 210 is used to capture 3D ultrasound images from an object, such as a patient 260 who needs a PICC operation for example. The image collecting unit 220 is used to receive the captured 3D ultrasound images from the ultrasound probe 210 and send them to the image processing unit 240 for the subsequent image processing. The data input unit 230 is used to input required data to the image processing unit 240 for the subsequent image processing as well. For example, the data input unit 230 may include a keyboard used to input required data. The image processing unit 240 is used to calculate 3D coordinates of a catheter (not shown) inserted in the patient 260 based on the captured 3D ultrasound images and the input required data. The monitor 250 is used to display detected results of the catheter and/or a corresponding blood vessel (not shown) in the 3D ultrasound images.

The image processing unit 240 may be programmed with software instructions stored in a non-transitory computer-readable medium, which, when executed by a processor, perform various operations of the apparatus 200. The computer-readable medium may include volatile and nonvolatile, removable and non-removable media implemented in any method or technology. The computer-readable medium includes, but is not limited to, RAM, ROM, EEPROM, flash memory, digital signal processor (DSP) or other memory technology, CD-ROM, digital versatile disks (DVD) or other optical storage, magnetic cassettes, magnetic tape, magnetic disk storage or other magnetic storage devices, or any other non-transitory medium which can be used to store the desired information and which can be accessed by an instruction execution system. The image processing unit 240 also may be implemented by hardware or firmware.

Figure 3:
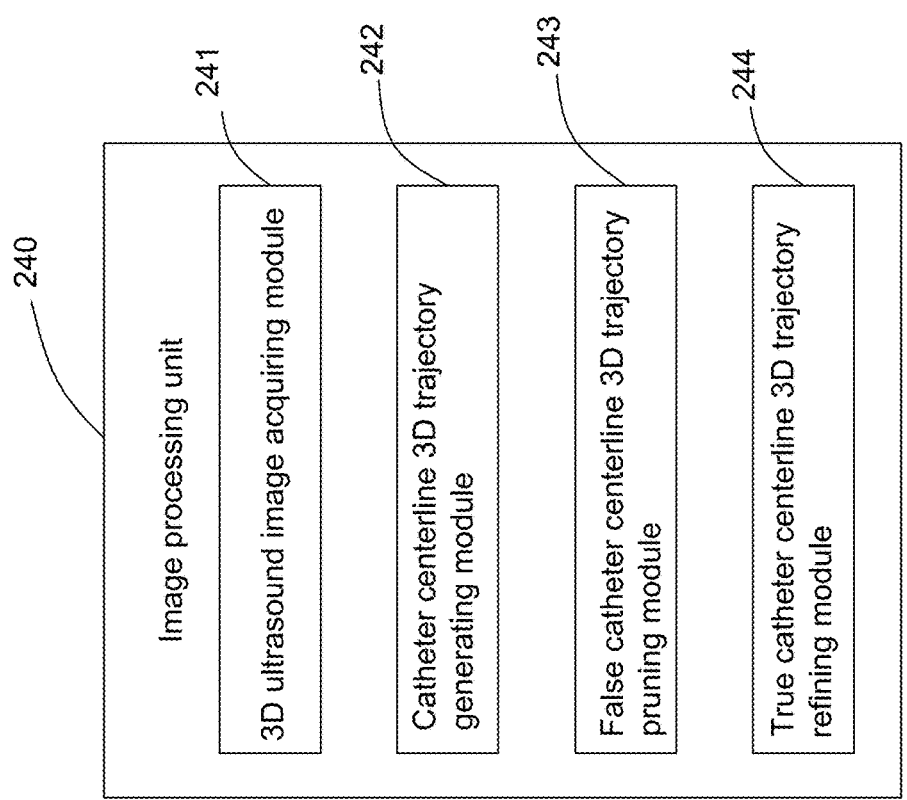
FIG. 3 is a part of a block diagram of an image processing unit of the apparatus of FIG. 2, according to one embodiment.

Referring to FIG. 3, a part of block diagram of the image processing unit 240, according to one embodiment is shown. The image processing unit 240 includes a 3D ultrasound image acquiring module 241, a catheter centerline 3D trajectory generating module 242, a false catheter centerline 3D trajectory pruning module 243, and a true catheter centerline 3D trajectory refining module 244. In one embodiment, these modules 241, 242, 243, and 244 of the image processing unit 240 may be situated in discrete modules and/or algorithms. In other embodiments, two or more of these modules 241, 242, 243, and 244 may be integrated together in a common module and/or algorithm.

Figure 4:
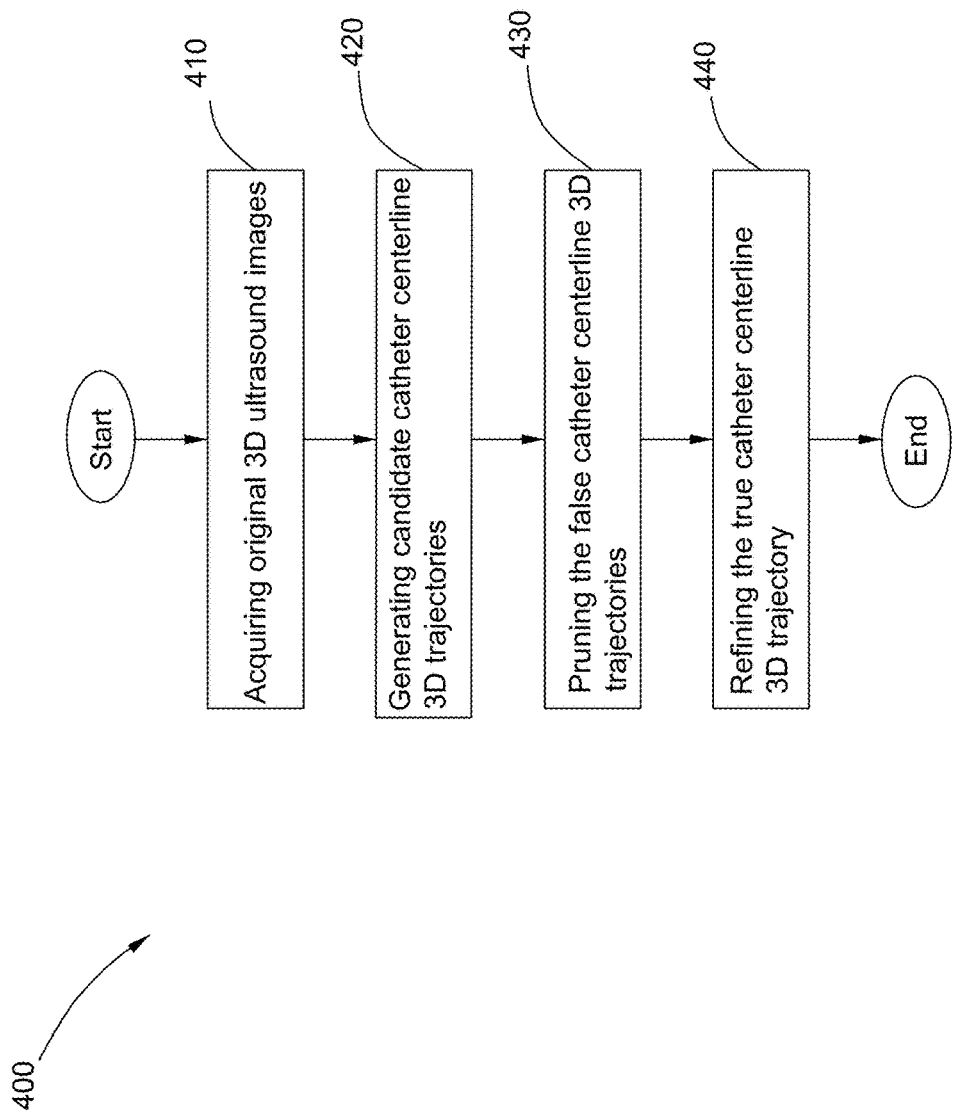
FIG. 4 is a flowchart of a method for detecting catheters in 3D ultrasound images, according to one embodiment.
Figure 5:
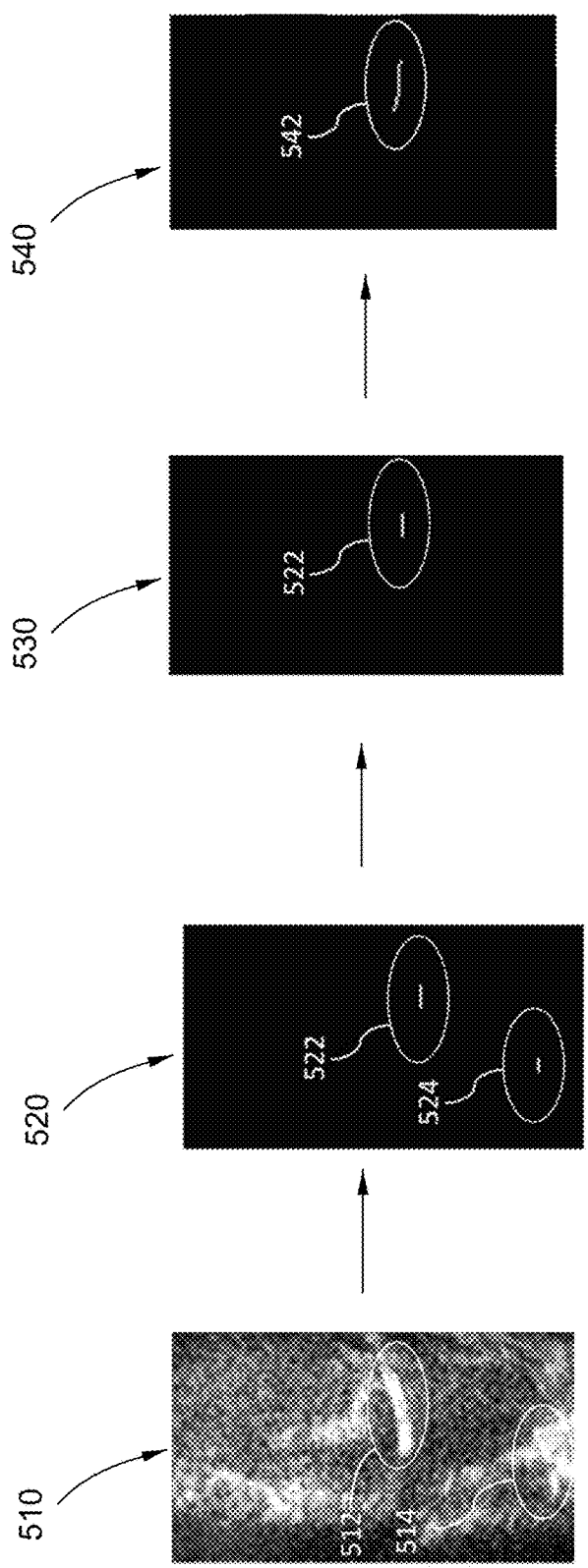
FIG. 5 is a schematic view of an exemplary process of the method of FIG. 4.

Referring to FIGS. 4 and 5, a flowchart of a method 400 and a schematic view of an exemplary process performed by the image processing unit 240 are shown, respectively. In one embodiment, the method 400 includes the following steps.

Step 410, the 3D ultrasound image acquiring module 241 of the image processing unit 240 acquires original 3D ultrasound images from the image collecting unit 220, for example an acquired 3D ultrasound image 510 is shown in FIG. 5. In general, the operator operates the ultrasound probe 210 to scan a region of interest (ROI) of the patient 260, which is located at the approximate position of the tip of the inserted catheter, and the catheter lies approximately in a horizontal scanning direction. For ease of illustration in drawings, most actual 3D images in drawings are shown as 2D images, such as the actual 3D image 510 shown as a 2D image in FIG. 5. As an example, the image 510 includes two candidate regions 512 and 514 where the catheter may be located.

In step 420, the catheter centerline 3D trajectory generating module 242 of the image process unit 240 generates several candidate catheter centerline 3D trajectories based on the acquired original 3D ultrasound images. For example, two candidate catheter centerline 3D trajectories 522 and 524 are generated, as shown in image 520 of FIG. 5, based on the original 3D ultrasound image 510 and predetermined input data. The predetermined data may include catheter dimensions, diameter of lumen or inner hole, patient information, etc. In other words, there may be one or more candidate catheter centerline 3D trajectories detected as candidate catheters, and then those candidates are re-detected to select a true catheter centerline 3D trajectory therefrom in the subsequent processing steps. In some embodiments, none of the candidates (522, 524) will be a true catheter centerline 3D trajectory through the subsequent processing steps, which means there is no catheter inserted in the blood vessel to be detected. For example, when the apparatus 200 is used to detect an inserted catheter, if the inserted catheter is moved to a wrong place by mistake, the detection result will show there is no catheter inserted, which may avoid some medical accidents.

In step 430, the false catheter centerline 3D trajectory pruning module 243 of the image process unit 240 prunes/deletes all false catheter centerline 3D trajectories from the candidate catheter centerline 3D trajectories. For example, the unit 240 prunes a false catheter centerline 3D trajectory 524 and selects another candidate 522 as the true catheter centerline 3D trajectory as shown in image 530 of FIG. 5. In some embodiments, when the number of the generated candidates of candidate catheter centerline 3D trajectories is equal to one and the shape detection of this one candidate strictly satisfies predetermined conditions, this step 430 may be omitted.

In step 440, the true catheter centerline 3D trajectory refining module 244 of the image process unit 240 refines the selected true catheter centerline 3D trajectory (for example, 522 in FIG. 5), which can improve the integrity of the true catheter centerline 3D trajectory. For example, 542 shown in image 540 of FIG. 5 shows a refined image of the true catheter centerline 3D trajectory. After image processing through the above four steps, a catheter centerline 3D trajectory is detected in real-time. Comparing step 420 with step 430, the image process requirement of step 430 is more restrict than the image process requirement of step 420, because step 430 only selects at most one candidate as the true catheter centerline 3D trajectory. However, comparing step 420 with step 440, the image process requirement of step 420 is more restrict than the image process requirement of step 440, because step 440 needs to achieve a more complete true catheter centerline 3D trajectory rather than a non-complete part of the true catheter centerline 3D trajectory detected in steps 420 and 430.

The steps 401, 402, 403, and 404 are four basic steps of this disclosed embodiment, and the detailed sub-steps thereof will be described in the latter paragraphs. When this method 400 is combined with other ultrasound image detection methods, such as a blood vessel ultrasound image method, a composite image showing both the catheter and the corresponding blood vessel can be calculated and shown through appropriate algorithms. Detailed descriptions of a blood vessel ultrasound image method can be found, for example, in a U.S. patent application Ser. No. 12/645,781, filed Dec. 23, 2009, "Methods for automatic segmentation and temporal tracking," to Patwardhan et al, which has the same assignee as this application. For ease of description, details of known method and algorithms applied in embodiments disclosed herein, such as Kalman filter, template matching, automatic segmentation and temporal tracking algorithms, for example, are not described herein. For example, a temporal tracking of the catheter can be calculated according to the temporal tracking algorithms disclosed in the U.S. patent application Ser. No. 12/645,781.

Figure 6:
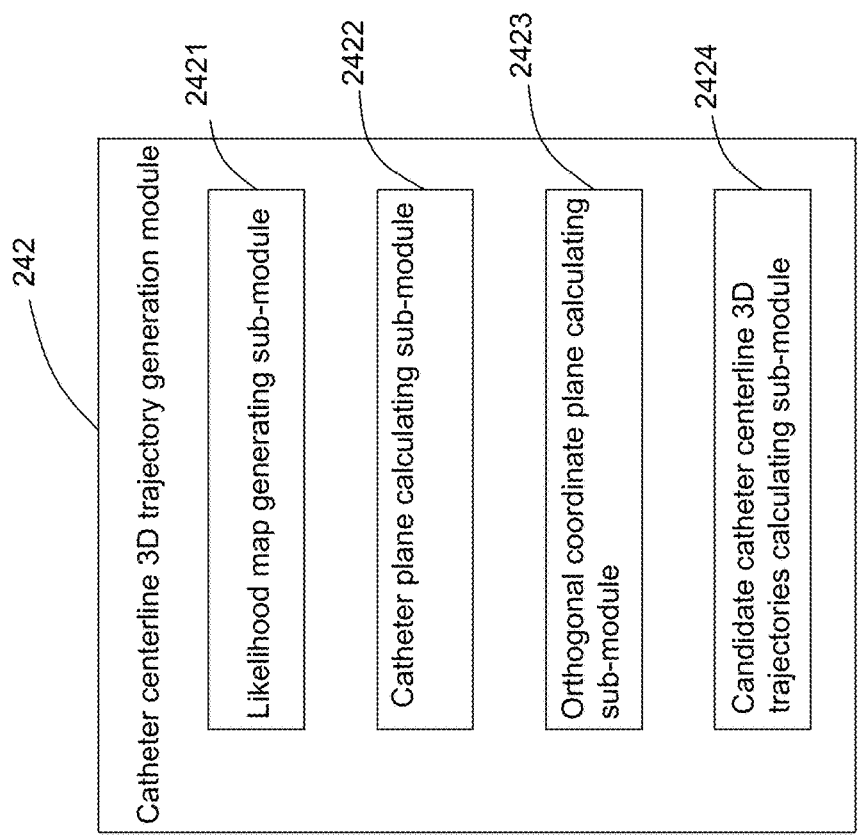
FIG. 6 is a block diagram of a catheter centerline 3D trajectory generation module of the image processing unit of FIG. 3, according to one embodiment.

Referring to FIG. 6, a block diagram of the catheter centerline 3D trajectory generation module 242, according to one embodiment is shown. The catheter centerline 3D trajectory generation module 242 includes a likelihood map generating sub-module 2421, a catheter plane calculating sub-module 2422, an orthogonal coordinate plane calculating sub-module 2423, and a candidate catheter centerline 3D trajectories calculating sub-module 2424. In one embodiment, these sub-modules 2421, 2422, 2423, and 2424 may be situated in discrete sub-modules and/or algorithms. In other embodiments, two or more of these sub-modules of the catheter centerline 3D trajectory generation module 242 may be integrated together in a common sub-module and/or algorithm.

Figure 7:
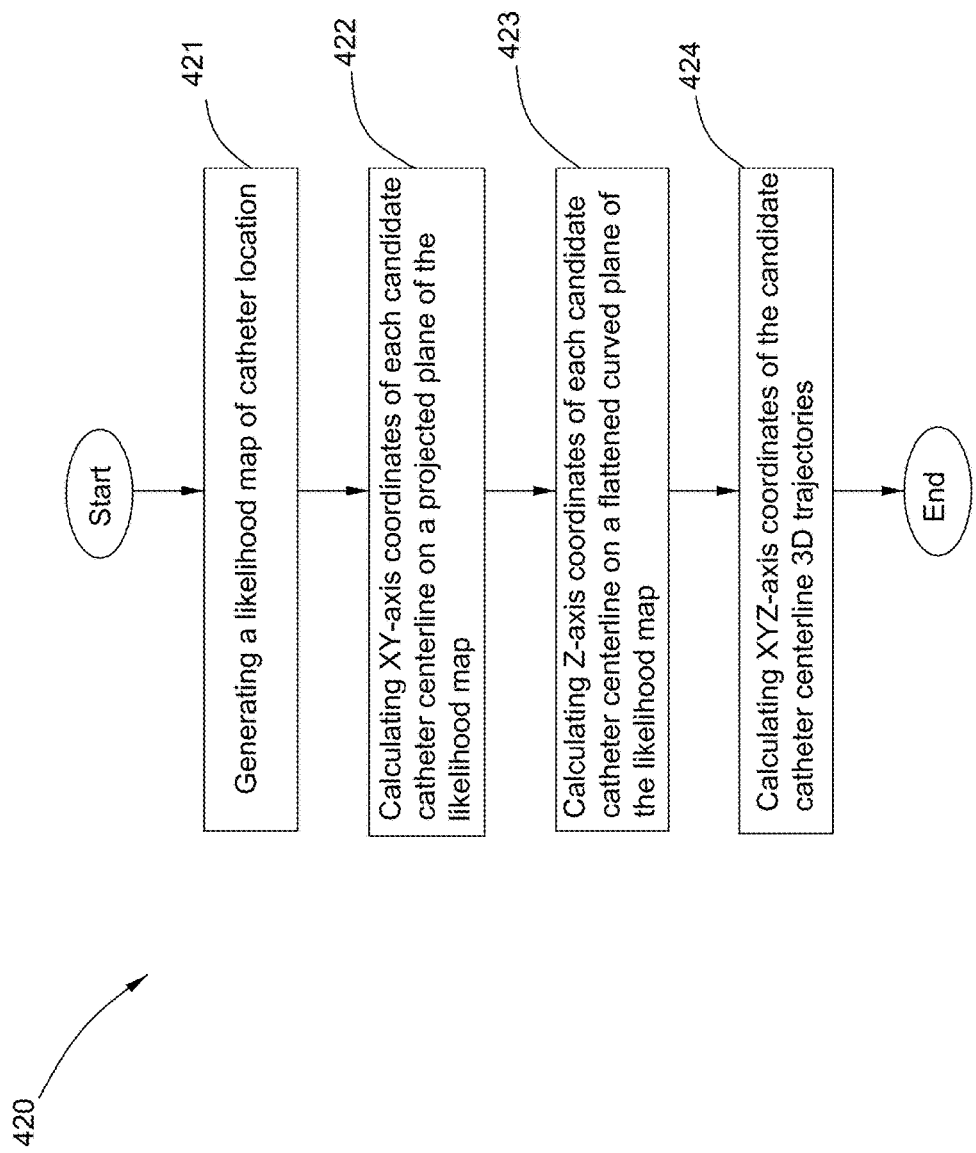
FIG. 7 is a flowchart of a method corresponding to the catheter centerline 3D trajectory generation module of FIG. 6, according to one embodiment.

In an embodiment, as shown in FIG. 7, a flowchart of a method 420 performed by the catheter centerline 3D trajectory generation module 242 is shown. In one embodiment, the method 420 includes step 421 for generating a likelihood map of catheter location performed by the likelihood map generating sub-module 2421. In step 422, XY-axis coordinates of each candidate catheter centerline on a projected plane of the likelihood map is calculated by the catheter plane calculating sub-module 2422. Z-axis coordinates of each candidate catheter centerline on a flattened curved plane of the likelihood map is calculated by the orthogonal coordinate plane calculating sub-module 2423 in step 423. In step 424, XYZ-axis coordinates (namely 3D trajectories) of the candidate catheter centerline 3D trajectories is calculated by the candidate catheter centerline 3D trajectories calculating sub-module 2424.

Figure 8:
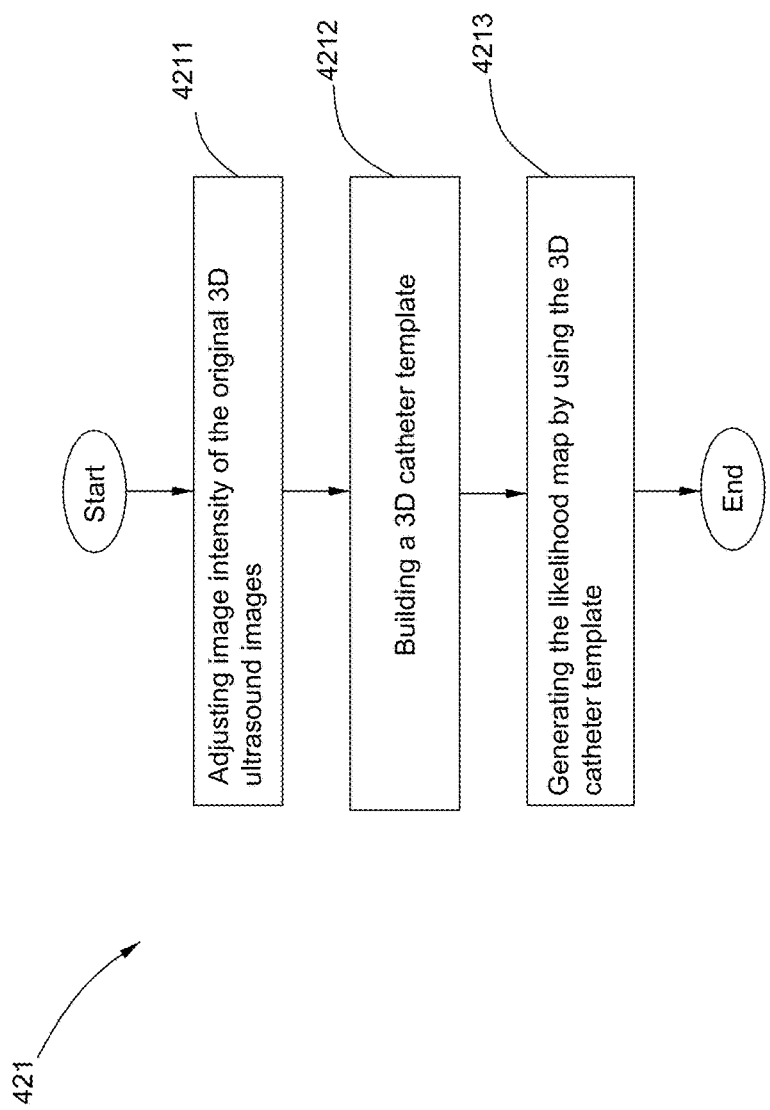
FIG. 8 is a flowchart of a method corresponding to a likelihood map generating sub-module of the catheter centerline 3D trajectory generation module of FIG. 6, according to one embodiment.
Figure 9:
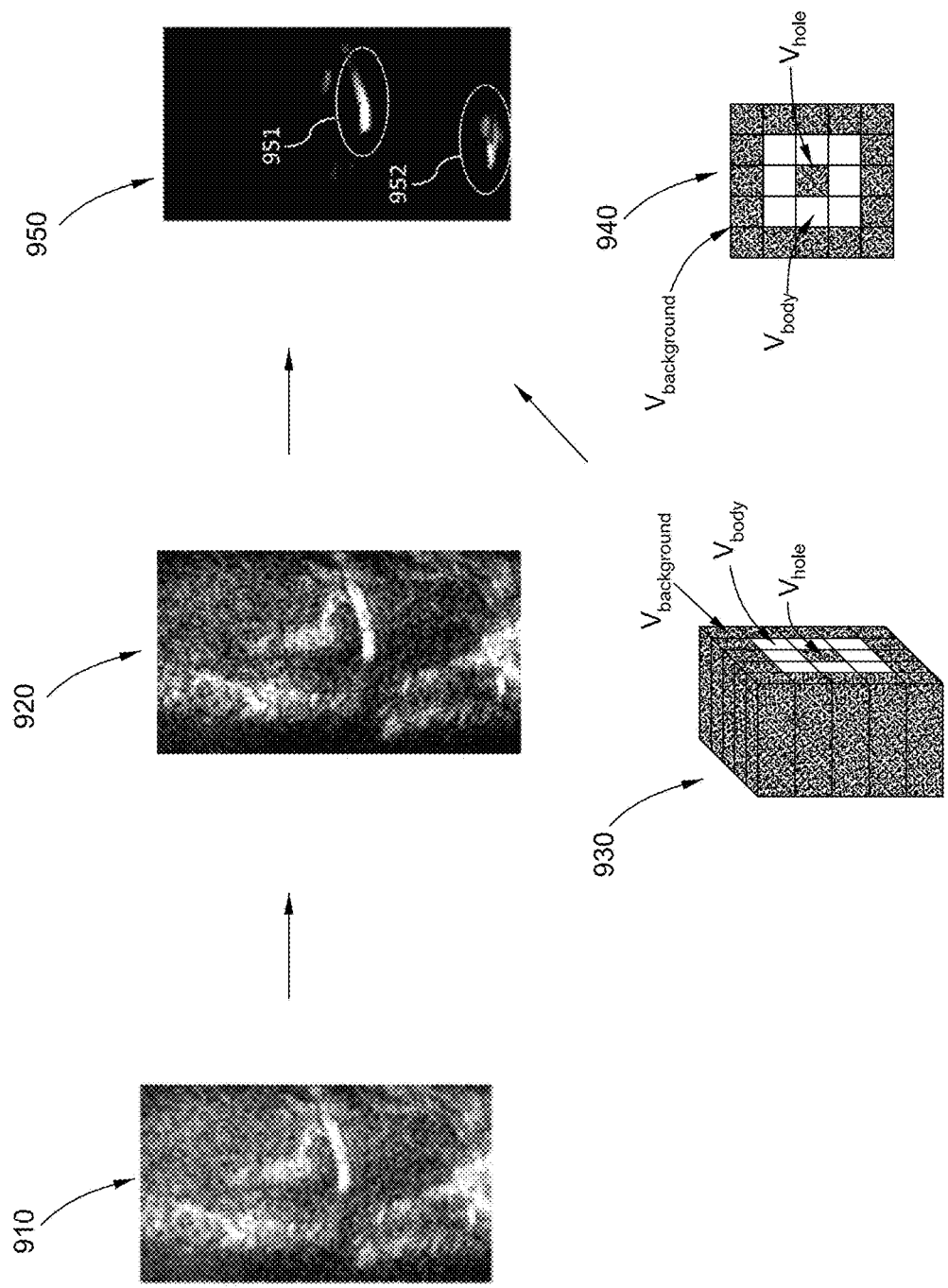
FIG. 9 is a schematic view of an exemplary process of the method of FIG. 8.

Referring to FIGS. 8 and 9, a detailed flowchart of step 421 and a schematic view of an exemplary process performed by the likelihood map generating sub-module 2421 are shown, respectively. In one embodiment, the step 421 includes the following sub-steps.

In step 4211, the original 3D ultrasound images are adjusted/rescaled. For example FIG. 9 shows an original 3D ultrasound image 910 and an adjusted 3D ultrasound image 920. The intensity contrast of the adjusted image 920 is greater than the intensity contrast of the original image 910. However, in order to avoid missing candidate catheter centerline 3D trajectories, the intensity contrast of image 920 is not much higher than the intensity contrast of image 910. In some embodiments, the original 3D ultrasound image 910 does not need to be adjusted, and thus, this step 4211 can be omitted.

In step 4212, a 3D catheter template 930 (940 is 930's front view) is built based on a specific acoustic signature and physical properties of the catheter when viewed under ultrasound, which may include specially designed catheters such as with air bubbles or wires placed at predetermined intervals, etc. In some embodiments, the physical properties of the catheter may include some geometric parameters of the catheter to be detected. For example, the geometric parameters of the catheter may include the diameter of the catheter body and the diameter of the catheter inner hole, which are input by the data input unit 230 (see FIG. 2). In some embodiments, the 3D catheter template 930 applies 3D cubical bars $V_{hole}$, $V_{body}$, and $V_{background}$ representing the catheter inner hole, the catheter body, and the catheter outside neighboring region, respectively. In other embodiments, the 3D cubical bars can be changed to other shapes, such as column-shaped and ring-shaped. The sizes of the 3D cubical bars $V_{hole}$, $V_{body}$ are built based on the input geometry parameters of the catheter from the data input unit 230.

The 3D cubical bars $V_{hole}$ and $V_{background}$ are defined as dark features, and the 3D cubical bars $V_{body}$ is defined as a bright feature in some embodiments.

In step 4213, a 3D likelihood map 950 (see FIG. 9) is generated based on the adjusted 3D ultrasound image 920 and the 3D catheter template 930. In some embodiments, the 3D ultrasound image 920 applies appropriate 3D template matching algorithms to search candidate catheters by using the 3D catheter template 930 matching in the adjusted 3D ultrasound image 920. A matching result M in a patch of the 3D ultrasound image 920 may be calculated as:

$$M = W_{bright}*S_{body}/\#V_{body} + W_{dark}*(S_{hole}+S_{background})/(\#V_{hole}\#V_{background}) \quad (1).$$

Where S represents the intensity sum of a region, #V represents the pixel number in a region, and W represents a weighting factor of the 3D catheter template 930. In one embodiment, $W_{bright}=1.0$ and $W_{dark}=-1.2$ in this step 4213, and thus an intensity contrast difference D1 between $W_{bright}$ and $W_{dark}$ is equal to $1.0-(-1.2)=2.2$. After matching all regions of the 3D ultrasound image 920 using the 3D catheter template 930, the 3D likelihood map 950 is generated, for example two candidate catheters 951 and 952 are searched and highlighted in the 3D likelihood map 950. In other words, the actual catheter may be located at one of the two candidate catheters 951 and 952. For ease of explanation, only two candidate catheters 951 and 952 are shown in the 3D likelihood map 950, but actually there may be more candidate catheters calculated in the 3D likelihood map or only one candidate catheter calculated in the 3D likelihood map.

Figure 10:
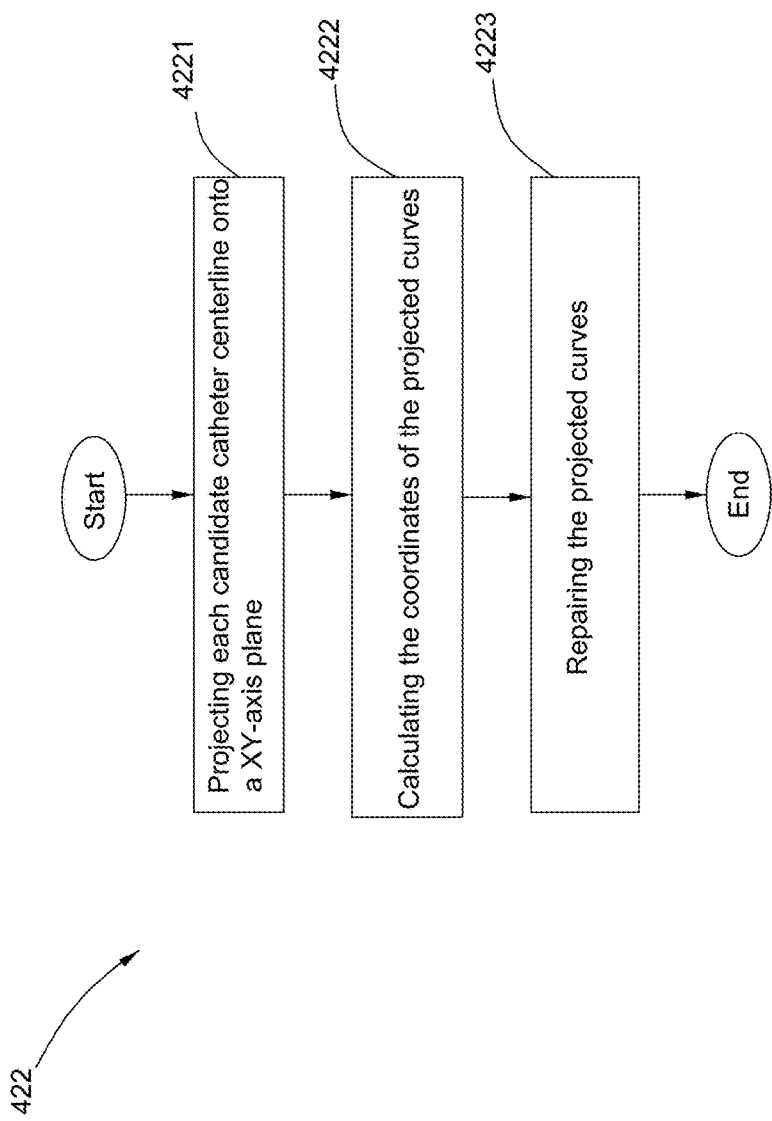
FIG. 10 is a flowchart of a method corresponding to a catheter plane calculating sub-module of the catheter centerline 3D trajectory generation module of FIG. 6, according to one embodiment.
Figure 11:
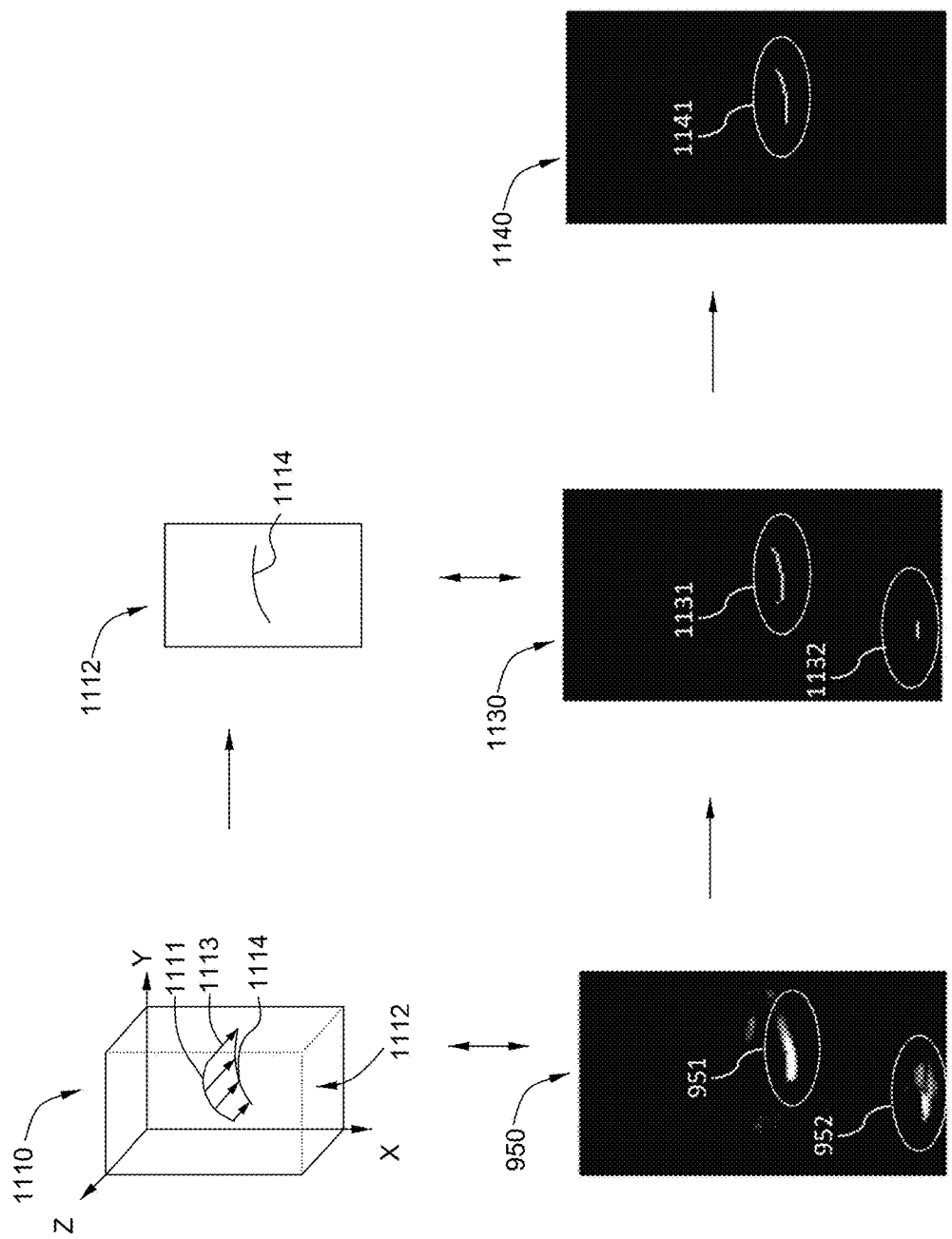
FIG. 11 is a schematic view of an exemplary process of the method of FIG. 10.

Referring to FIGS. 10 and 11, a detailed flowchart of step 422 and a schematic view of an exemplary process performed by the catheter plane calculating sub-module 2422 are respectively shown. In one embodiment, step 422 includes the following sub-steps.

In step 4221, a catheter centerline of each of the candidate catheters 951 and 952 of the 3D likelihood map 950 are projected onto a catheter plane such as a XY-axis plane. According to a coordinate setting shown as a 3D image 1110 in FIG. 11, a catheter centerline 1111 is assumed to extend along the Y-axis and cross each XZ-axis plane at most once. The catheter centerline 1111 can be projected onto a XY-axis plane 1112 along projecting lines 1113 and then a projected curve 1114 is projected onto the XY-axis plane 1112. Similarly, based on a projection algorithm, a catheter centerline of each candidate catheter (951 and 952) of the 3D likelihood map 950 can be projected onto a XY-axis plane 1130. In one embodiment, each 2D XZ-axis slice is extracted from the 3D image 950, and the voxel point having the maximum intensity value on each 2D XZ-axis slice is selected, and all selected voxel points of all 2D XZ-axis slices are connected together as the catheter centerline of each candidate catheter (951 and 952), and then these catheter centerlines are projected onto the XY-axis plane 1130, such as two projected curves 1131 and 1132 are generated in the XY-axis plane 1130, for example.

In step 4222, the coordinates of the projected curves 1131 and 1132 in the 3D likelihood map 950 are calculated. In one embodiment, the coordinates of the projected curves 1131 and 1132 are calculated using appropriate algorithms, such as Hough Transform. In some embodiments, during this step, some false projected curves (1132) may be rejected by setting some rejection conditions. For example, when the length of a projected curve is less than a predetermined value, this projected curve may be rejected in this step, such as the curve 1132 is rejected and not shown in an updated XY-axis plane 1140. In other embodiments, the rejection conditions can be changed according to requirements, such as when the slant angle of a projected curve is greater than a predetermined value (such as 30 degrees), this projected curve may be rejected in this step.

In step 4223, the projected curves (1131) in the 3D likelihood map 950 are repaired to become complete curves. In some embodiments, the projected curve 1131 may not be complete, for example, maybe one or more voxel points are missed during the step 4222, and the projected curve 1131 is repaired by appropriate algorithms, such as polynomial curve fitting algorithms or the like. After repairing the projected curves 1131, the complete coordinates of the updated projected curve 1141 shown in the updated XY-axis plane 1140 are determined. Namely, the XY-axis coordinates of a centerline of each candidate catheter 951 in the 3D likelihood map 950 are determined through above steps.

Figure 12:
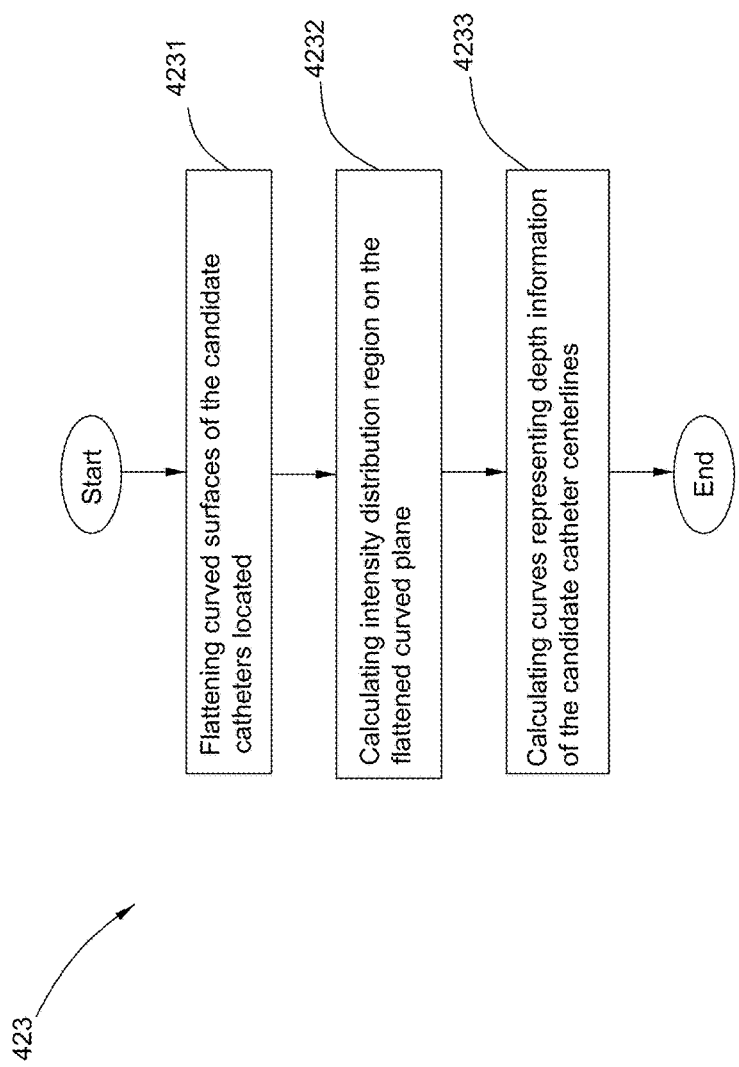
FIG. 12 is a flowchart of a method corresponding to an orthogonal coordinate plane calculating sub-module of the catheter centerline 3D trajectory generation module of FIG. 6, according to one embodiment.
Figure 13:
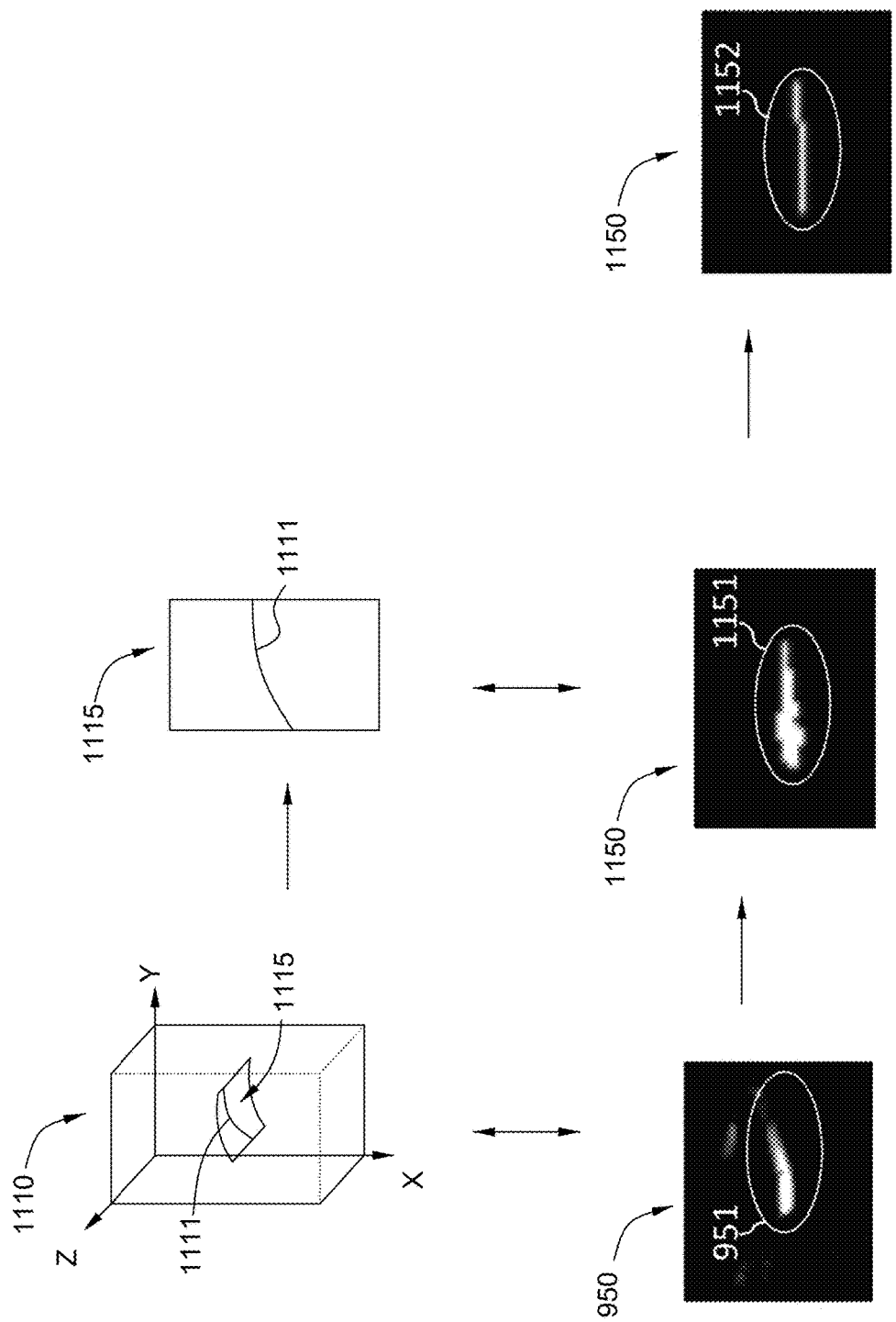
FIG. 13 is a schematic view of an exemplary process of the method of FIG. 12.

Referring to FIGS. 12 and 13, a detailed flowchart of step 423 and a schematic view of an exemplary process performed by the orthogonal coordinate plane calculating sub-module 2423 are respectively shown. In one embodiment, step 423 includes the following sub-steps.

In step 4231, a curved surface of each of the candidate catheters (951) of the 3D likelihood map 950 is flattened. According to the 3D image 1110 shown in FIG. 13, a curved surface 1115 by which the catheter centerline 1111 is located can be determined based on the projecting lines 1113 shown in FIG. 11, and then the curved surface 1115 is flattened, which is shown to the right of the 3D image 1110. Similarly, flattened curved planes (1150), which the corresponding candidate catheters (951) located, are calculated based on the above step 422.

In step 4232, an intensity distribution region (1151) of each of the candidate catheters (951) of the 3D likelihood map 950 on the corresponding flattened curved plane (1150) is calculated. The calculation method is similar to the step 4222 such as by using Hough Transform, and thus not described again. In some embodiments, during this step, some false intensity distribution regions may be rejected through setting some rejection conditions. For example, when the ratio between the long axis and the short axis of an intensity distribution region is less than a predetermined value, this intensity distribution region may be rejected in this step. In other embodiments, the rejection conditions can be changed according to requirements.

Step 4233, a curve 1152 representing depth information of a catheter centerline of each candidate catheter 951 of the 3D likelihood map 950 is calculated on the flattened curved plane 1150 based on the corresponding intensity distribution region 1151. The curve 1152 may be calculated by appropriate algorithms, such as by using polynomial curve fitting algorithms to extract a longest curve 1152 from the corresponding intensity distribution region 1151. After determining the curve 1152 from the corresponding intensity distribution region 1151, the complete coordinates of the curve 1152 shown in the flattened curved plane 1150 are determined. Namely, the Z-axis coordinates of each candidate catheter centerline 951 in the 3D likelihood map 950 are determined.

After getting the XY-axis coordinates and Z-axis coordinates of each candidate catheter centerline 951, all of the candidate catheter centerline 3D trajectories are determined by the candidate catheter centerline 3D trajectories calculating sub-module 2424. In some embodiments, operators may determine which one of the candidate catheter centerline 3D trajectories is the true catheter centerline 3D trajectory from the calculated candidate catheter centerline 3D trajectories based on their experience, and then other candidate catheter centerline 3D trajectories as false cases are omitted accordingly. However, when the operators cannot determine which of the candidate catheter 3D trajectories is the true one, they cannot directly apply those detected candidate catheter centerline 3D trajectories to guide them during the operations. For automatically determining which one of the candidate catheter centerline 3D trajectories is the true catheter centerline 3D trajectory, the following paragraphs will describe more detailed embodiments of the steps 430 and 440.

Figure 14:
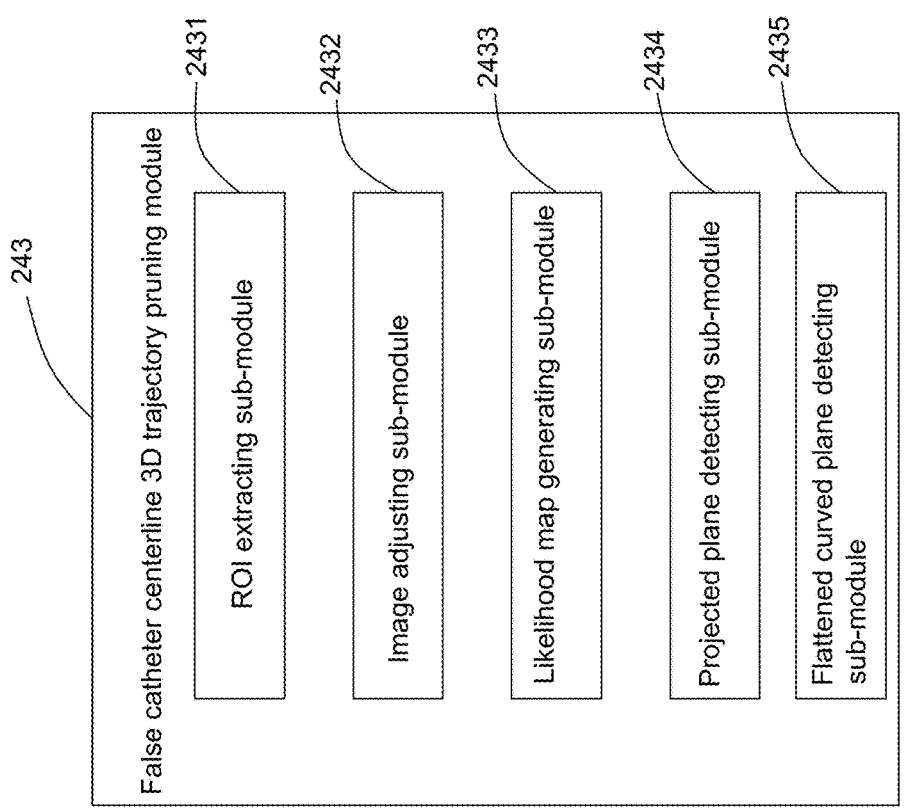
FIG. 14 is a block diagram of a false catheter centerline 3D trajectory pruning module of the image processing unit of FIG. 3, according to one embodiment.

Referring to FIG. 14, a block diagram of the false catheter centerline 3D trajectory pruning module 243, according to one embodiment is shown. The false catheter centerline 3D trajectory pruning module 243 includes a ROI extracting sub-module 2431, an image adjusting sub-module 2432, a likelihood map generating sub-module 2433, a projected plane detecting sub-module 2434, and a flattened curved plane detecting sub-module 2435. In one embodiment, these sub-modules 2431, 2432, 2433, 2434, and 2435 may be situated in discrete sub-modules and/or algorithms. In other embodiments, two or more of these sub-modules of the false catheter centerline 3D trajectory pruning module 243 may be integrated together in a common sub-module and/or algorithm.

Figure 15:
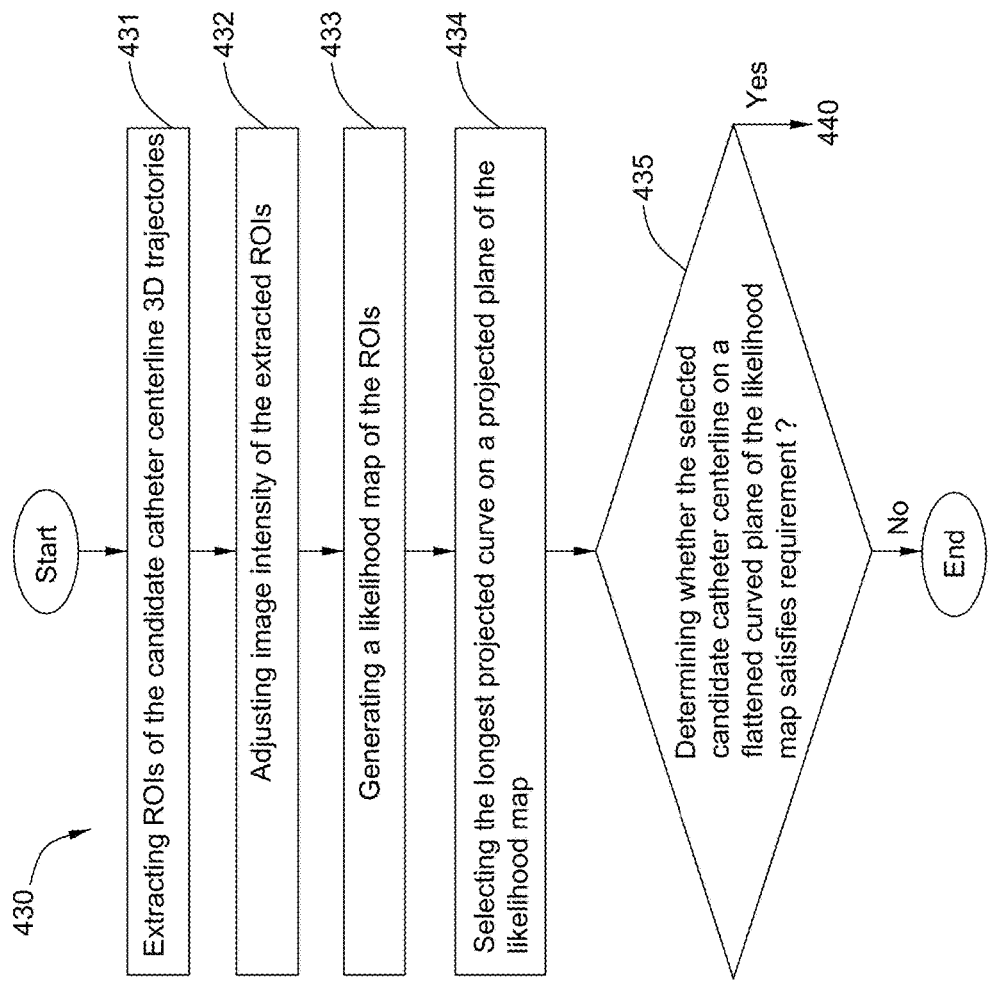
FIG. 15 is a flowchart of a method corresponding to the false catheter centerline 3D trajectory pruning module of FIG. 14, according to one embodiment.
Figure 16:
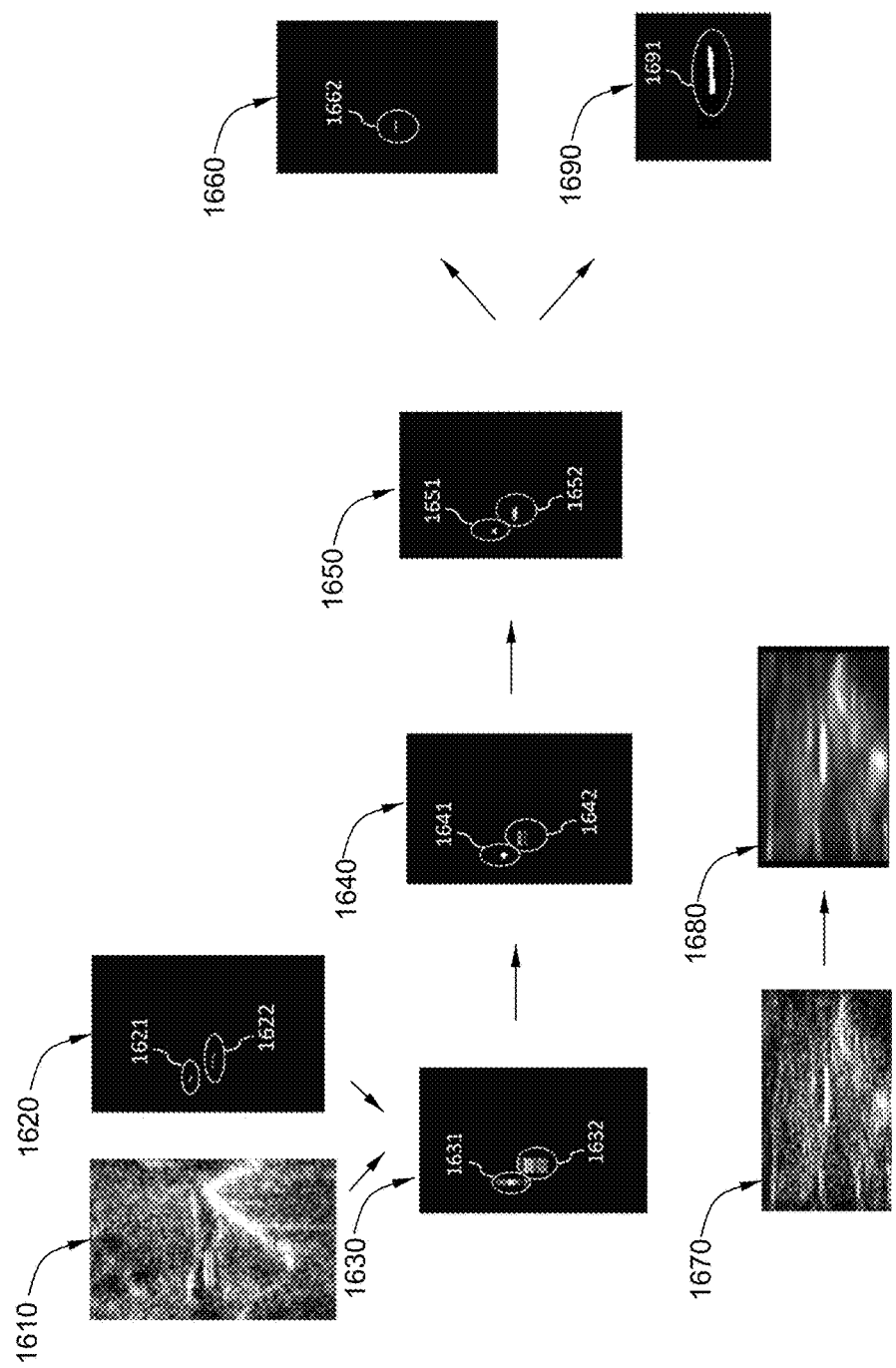
FIG. 16 is a schematic view of an exemplary process of the method of FIG. 15.

Referring to FIGS. 15 and 16, a flowchart of a method 430 and a schematic view of an exemplary process performed by the false catheter centerline 3D trajectory pruning module 243 is shown. In an embodiment, the method 430 includes the following steps.

In step 431, ROIs of the candidate catheter centerline 3D trajectories" are extracted from the original 3D ultrasound image based on the calculated candidate catheter 3D trajectories, performed by the ROI extracting sub-module 2431. The ROIs include the candidate catheter 3D trajectories themselves and the neighborhood regions thereof. The ranges of the neighborhood regions of the candidate catheter 3D trajectories can be changed according to different requirements. For example, FIG. 16 shows an original 3D ultrasound image 1610 and a calculated image 1620 including two candidate catheter centerline 3D trajectories 1621 and 1622 based on the method 420. Two ROIs 1631 and 1632 in the image 1630 are extracted from the original 3D ultrasound image 1610 according to the calculated image 1620 and the predetermined range of the neighborhood regions.

In step 432, the ROIs 1631 and 1632 in the image 1630 are adjusted/rescaled performed by the image adjusting sub-module 2432. For example, FIG. 16 shows an adjusted 3D ultrasound image 1640 with two adjusted ROIs 1641 and 1642. The intensity contrast of image 1630 is greater than the intensity contrast of image 1640, which can easily process the adjusted image 1640 in the subsequent processes. For improving precision, the intensity contrast of image 1640 is much higher than the intensity contrast of image 1630, compared with the image adjustment of step 4211. In some embodiments, the image 1630 does not need to be adjusted, and thus, this step 432 can be omitted accordingly.

In step 433, a likelihood map of the ROIs 1641 and 1642 is generated by the likelihood map generating sub-module 2433. The likelihood map generation method is similar to step 421, and thus not described again. For example, a likelihood map 1650 is generated and includes two candidate catheter centerlines 1651 and 1652. However, the parameters $W_{bright}$ and $W_{dark}$ are different from the step 421. In this step 433, for pruning all false catheters, an intensity contrast difference D2 between $W_{bright}$ and $W_{dark}$ of the equation (1) is greater than the intensity contrast difference D1. In one embodiment, $W_{bright}=1.0$ and $W_{dark}=-3.0$ in this step 433, and thus the intensity contrast difference D2 is equal to $1.0-(-3.0)=4.0$.

In step 434, a longest projected curve 1662 on a projected plane 1660 of the likelihood map 1650, corresponding to a candidate catheter centerline 1652 (1651 is deleted), is selected by the projected plane detecting sub-module 2434. Similar to step 422, all of the candidate catheter centerlines on corresponding projected planes of the likelihood map can be determined in a manner similar to that in step 422, and thus, not described again. And then the longest projected curve of all of the candidate catheter centerlines on corresponding projected planes can be selected by using appropriate algorithms.

In step 435, it is determined whether an intensity distribution region 1691 on a flattened curved plane 1690 of the likelihood map 1650, corresponding to the selected longest candidate catheter centerline 1652, satisfies predetermined catheter shape requirements performed by the flattened curved plane detecting sub-module 2435. Similar to step 423, the intensity distribution region 1691 can be calculated in a manner similar to that in step 423, and thus, not described again. If the intensity distribution region 1691 satisfies catheter shape requirements, the candidate catheter centerline 1652 is determined as the true catheter centerline. If the intensity distribution region 1691 does not satisfy the requirements, the candidate catheter centerline 1652 is also determined as a false catheter centerline, i.e., there is no catheter inserted in the detected patient 260. For example, when the ratio between the long axis and the short axis of the intensity distribution region 1691 is less than a predetermined value, this intensity distribution region 1691 may be rejected in this step. In other embodiments, the rejection conditions can be changed according to requirements.

In some embodiments, before extracting the ROIs, a corresponding original 3D ultrasound image 1670 may be first smoothed through appropriate algorithms, such as utilizing a probabilistic speckle model using Fisher-Tippett distribution and computing a reflectivity parameter for all voxels using a small 3D patch around them, to generate a smoothed 3D ultrasound image 1680. And then the intensity distribution region 1691 on the flattened curved plane 1690 of the likelihood map 1650 is generated based on the smoothed 3D ultrasound image 1680, which can increase the determining precision in step 435. After these steps 431-435, a true catheter 3D trajectory (1652) may be determined.

Figure 17:
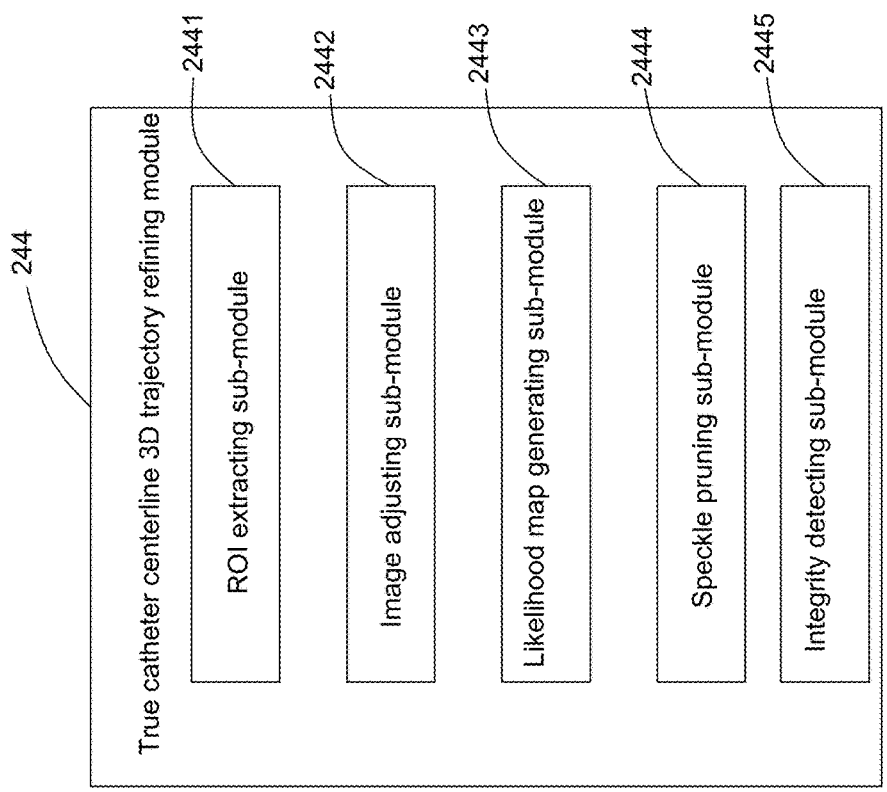
FIG. 17 is a block diagram of a true catheter centerline 3D trajectory refining module of the image processing unit of FIG. 3, according to one embodiment.

Referring to FIG. 17, a block diagram of the true catheter centerline 3D trajectory refining module 244, according to one embodiment is shown. The true catheter centerline 3D trajectory refining module 244 includes a ROI extracting sub-module 2441, an image adjusting sub-module 2442, a likelihood map generating sub-module 2443, a speckle pruning sub-module 2444, and an integrity detecting sub-module 2445. In one embodiment, these sub-modules 2441, 2442, 2443, 2444, and 2445 may be situated in discrete sub-modules and/or algorithms. In other embodiments, two or more of these sub-modules of the true catheter centerline 3D trajectory refining module 244 may be integrated together in a common sub-module and/or algorithm.

Figure 18:
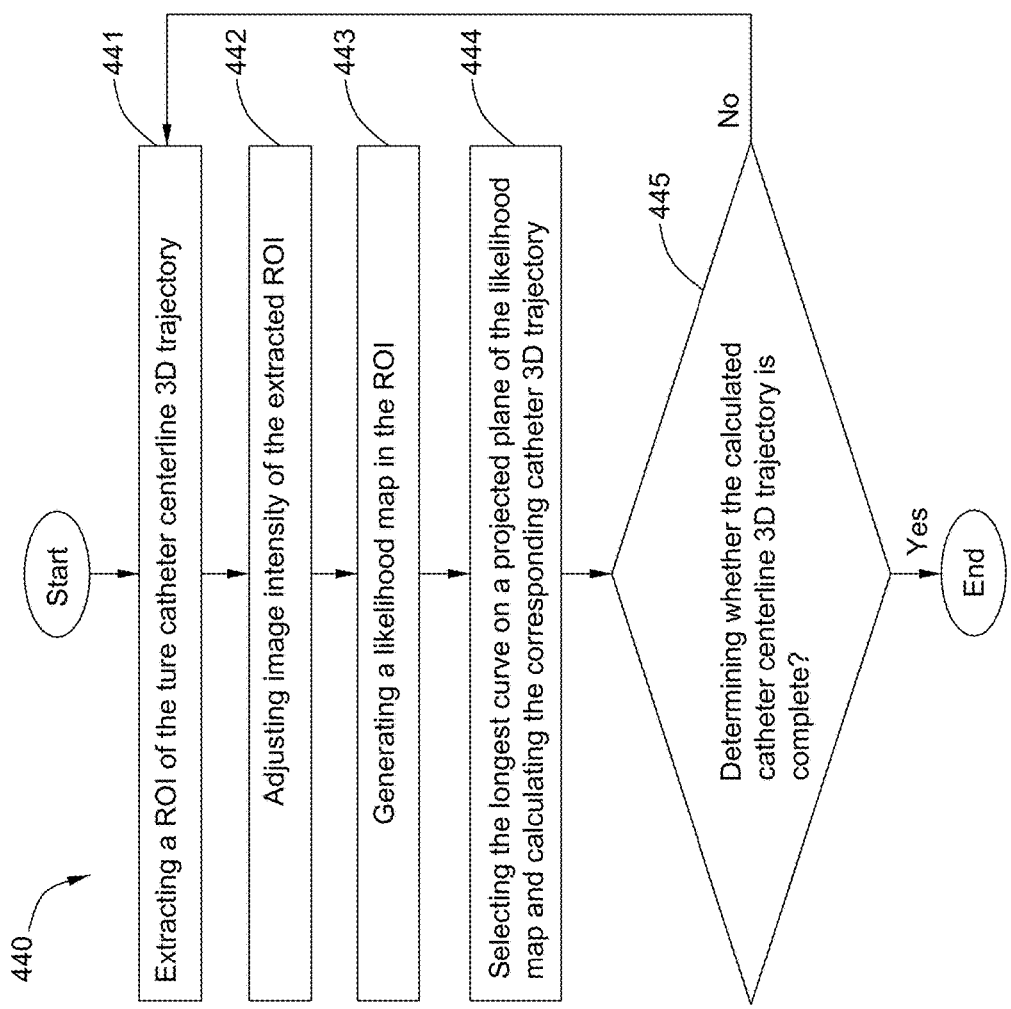
FIG. 18 is a flowchart of a method corresponding to the true catheter centerline 3D trajectory refining module of FIG. 17, according to one embodiment.
Figure 19:
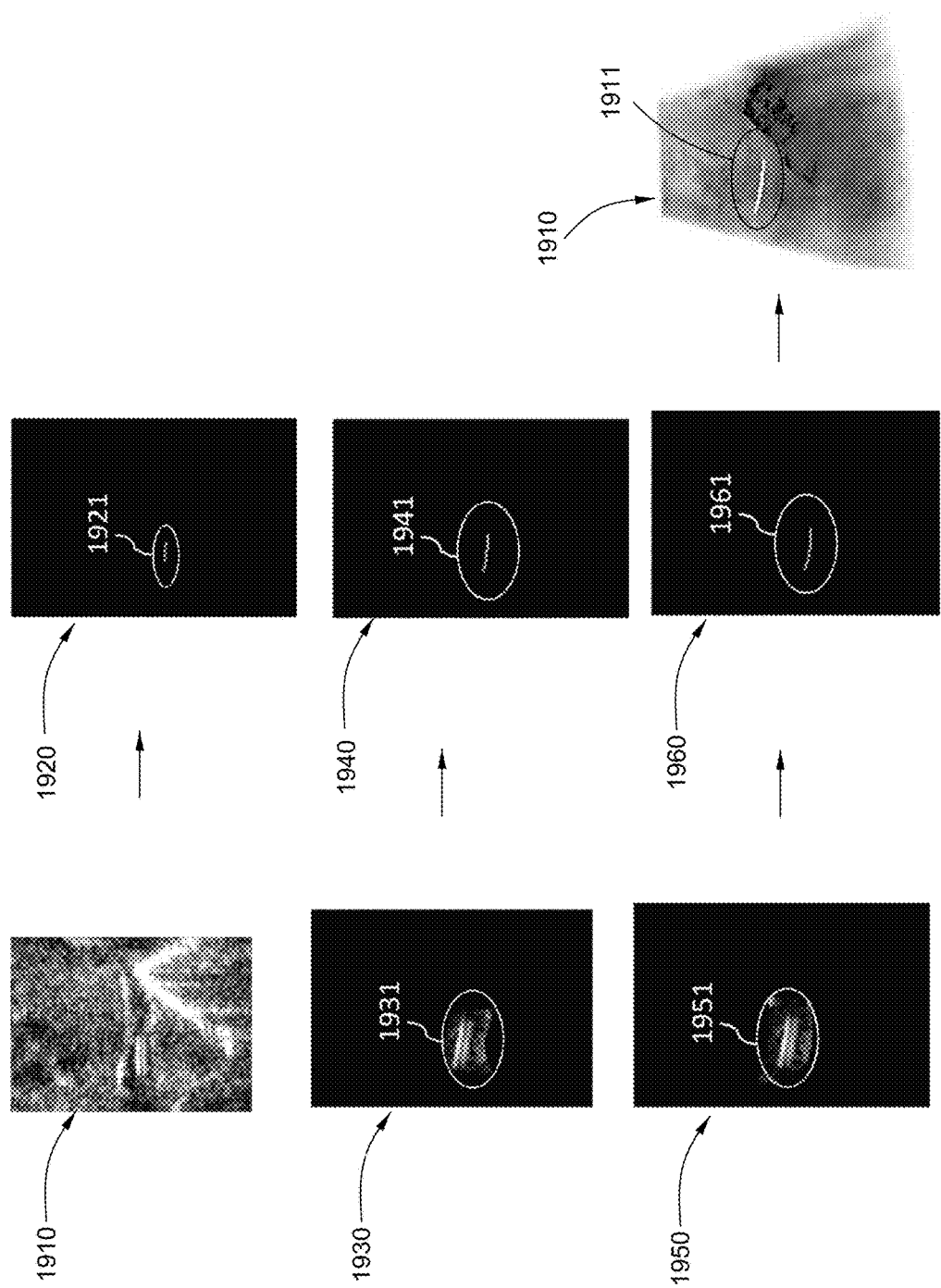
FIG. 19 is a schematic view of an exemplary process of the method of FIG. 18.

Referring to FIGS. 18 and 19, a flowchart of a method 440 and a schematic view of an exemplary process performed by the true catheter centerline 3D trajectory refining module 244 is shown. In one embodiment, the method 440 includes the following steps:

In step 441, a ROI of the selected true catheter centerline 3D trajectory is extracted from the original 3D ultrasound image by the ROI extracting sub-module 2441. The ROI includes the true catheter 3D trajectory itself and the neighborhood regions thereof. The ranges of the neighborhood regions of the true catheter 3D trajectory can be changed according to different requirements. For example, FIG. 19 shows an original 3D ultrasound image 1910 and a calculated image 1920 including a true catheter 3D trajectory 1921 based on the method 430. A ROI 1931 in the image 1930 is extracted from the original 3D ultrasound image 1910 according to the calculated image 1920 and the predetermined range of the neighborhood regions. In general, the predetermined range of the neighborhood regions in this step is greater than the predetermined range of the neighborhood regions in the step 431.

In step 442, the ROI 1931 in the image 1930 is adjusted/rescaled performed by the image adjusting sub-module 2442. This step is similar to the step 432, and thus not described again and no schematic views are shown. However, the adjusting degree of intensity contrast in this step may be less than that in the step 432. In some embodiments, the image 1930 does not need to be adjusted, and thus, this step 442 can be omitted accordingly.

In step 443, a likelihood map of the ROI 1931 is generated by the likelihood map generating sub-module 2443. The likelihood map generation method is similar to steps 421 and 433, and thus not described again. However, the parameters $W_{bright}$ and $W_{dark}$ are different from the step 421 and step 433. In this step 443, for achieving a complete true catheter centerline 3D trajectory, the intensity contrast difference D3 between $W_{bright}$ and $W_{dark}$ the equation (1) is less than the intensity contrast difference D1. In one embodiment, $W_{bright}=1.0$ and $W_{dark}=-1.0$ in this step 443, and thus, the intensity contrast difference D2 is equal to 1.0−(−1.0)=2.0. Namely, D3<D1<D2, i.e., the intensity contrast difference requirement of achieving the likelihood map in step 433 is the most restrict step, and the step 443 is the least restrict step.

In step 444, a longest projected curve 1941 on a projected plane 1940 of the likelihood map (not shown) is selected by the speckle pruning sub-module 2444. This step is similar to the step 434, and thus, not described again and no schematic views are shown. Because to some speckles/noises (not shown) may be detected on the projected plane 1940 in the step 443, the speckles need to be deleted in this step 444. In some embodiments, this step 444 may be omitted. Then, a true catheter 3D trajectory including XYZ-axis coordinates corresponding to the selected longest projected curve 1941 is determined based on above mentioned steps.

In step 445, it is determined whether the calculated true catheter centerline 3D trajectory is whether it is a complete catheter centerline 3D trajectory performed by the integrity detecting sub-module 2445. If the calculated true catheter centerline 3D trajectory is complete, based on some predetermined conditions, the process ends. If the calculated true catheter centerline 3D trajectory is not complete, based on those predetermined conditions, the process goes back to step 441 to re-calculate/update the true catheter centerline 3D trajectory based on more than one time of calculating under different image parameter settings. In some embodiments, the predetermined conditions may include the following three conditions. First, when the repeating/iterative times from step 441 to step 444 is greater than a predetermined value, such as ten, the process ends. Second, when the detection length on XY-axis plane of the true catheter centerline 3D trajectory is not increased between two consecutive repeating steps (441 to 444), the process ends. Third one, when the difference of two detection lengths on XY-axis plane or on ZY-axis plane of the true catheter centerline 3D trajectory in two consecutive repeating steps (441 to 444) is greater than a predetermined value, namely changed extremely in the two consecutive detections, the process ends. In other embodiments, the predetermined conditions may vary according to requirements.

After the process ends, a final true catheter centerline 3D trajectory is determined. For example, the projected curve 1941 on the projected plane 1940 is calculated from the ROI 1931 of the image 1930 in a first time of the detection from step 441 to step 444, and a projected curve 1961 on a projected plane 1960 is calculated from a ROI 1951 of an image 1950 in a second time of the detection from step 441 to step 444. In step 445, the projected curve 1961 is compared with the projected curve 1941, if the projected curve 1961 is the same as the projected curve 1941, then the process ends. Then, the projected curve 1941 will act as the final detection result, and thus, a true catheter centerline 3D trajectory 1911 in a 3D ultrasound image 1910 will be calculated based on above mentioned methods. The image processing unit 240 can output the result data to the monitor 250 to display the true catheter centerline 3D trajectory 1911 in the 3D ultrasound image 1910. On the other hand, if the projected curve 1961 is a little longer than the projected curve 1941, then the process goes back to the step 441, to re-calculate/update the true catheter centerline 3D trajectory until the updated one is the same as the previous one. Or, if the projected curve 1961 is extremely different from the projected curve 1941 based on the predetermined conditions, the process ends, and then the projected curve 1941 will act as the final detection result, and be used to calculate the final/refined true catheter centerline 3D trajectory 1911.

In some embodiments, for example when the detection requirement is not high, the true catheter centerline 3D trajectory refining module 244 may be deleted. The true catheter centerline 3D trajectory refining module 244 is used to obtain the selected true catheter centerline 3D trajectory with greater accuracy and completeness, which can better guide the operators.

Figure 20:
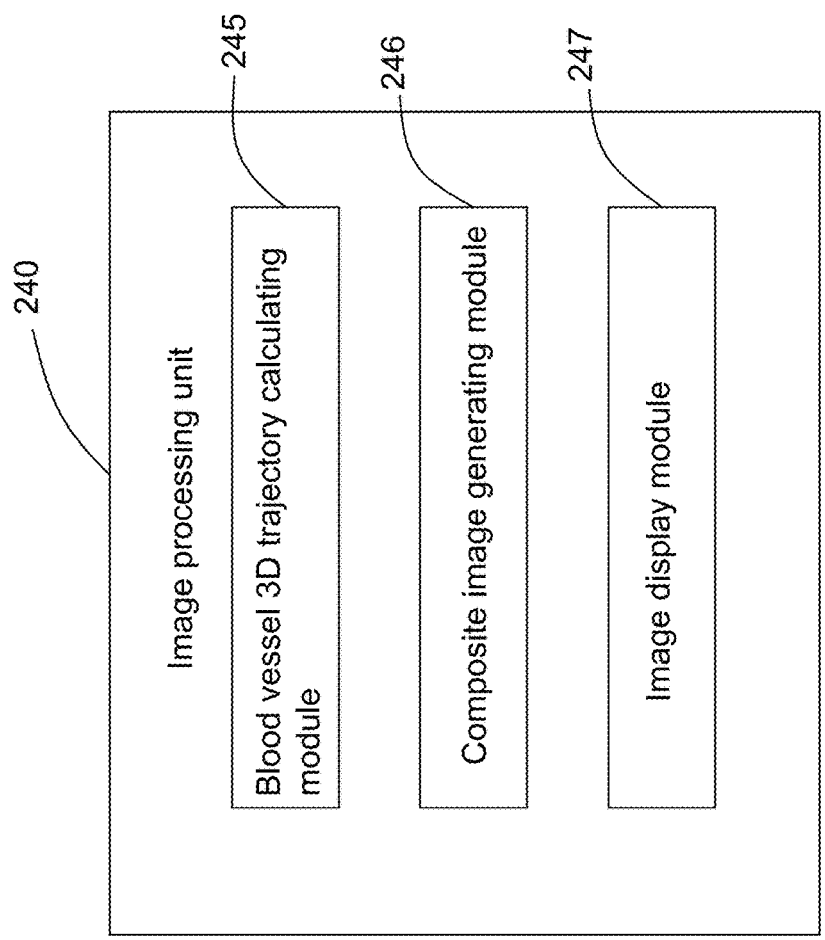
FIG. 20 is the other part of block diagram of the image processing unit of FIG. 2, according to one embodiment.

Referring to FIG. 20, the image processing unit 240 may further include a blood vessel 3D trajectory calculating module 245, a composite image generating module 246, and an image display module 247. The blood vessel 3D trajectory calculating module 245 is used to calculate the 3D trajectory of the blood vessel in which the catheter is inserted. The methods of calculating the 3D trajectory of the blood vessel have been previously proposed, such as in U.S. patent application Ser. No. 12/645,781 mentioned before or other conventional methods, and thus, not described here. The catheter is highlighted in a manner to render the image of the catheter clear to a user or operator.

Figure 21:
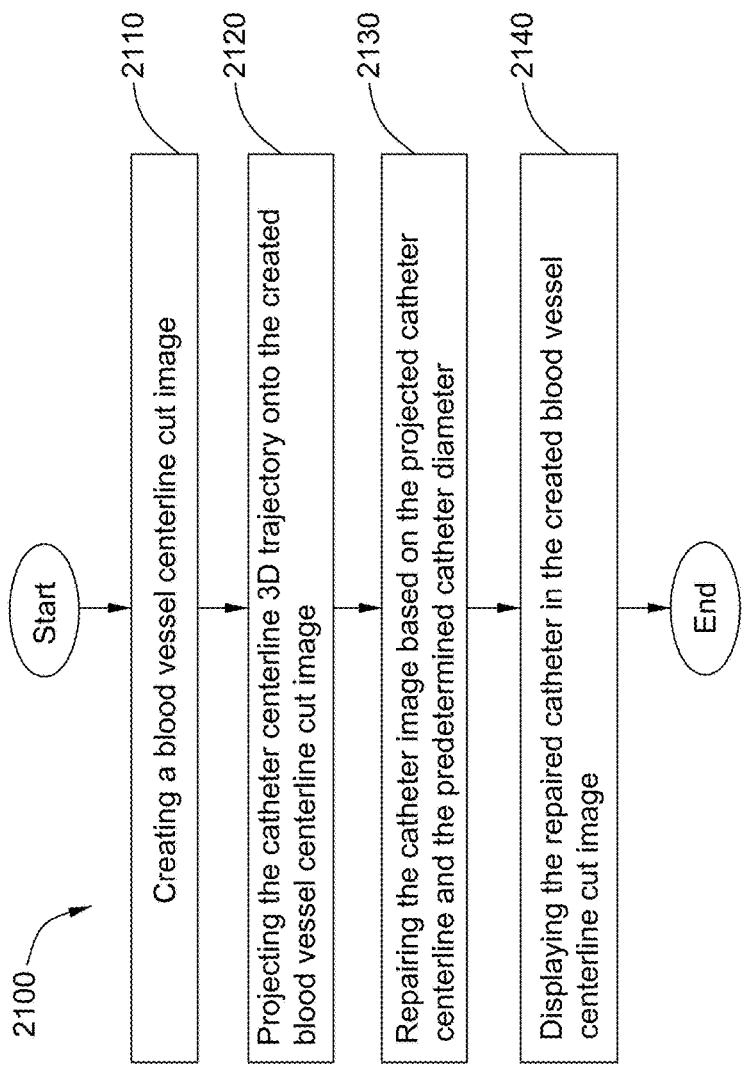
FIG. 21 is a flowchart of a method corresponding to a composite image generating module and an image display module of the image processing unit of FIG. 20, according to one embodiment.
Figure 22:
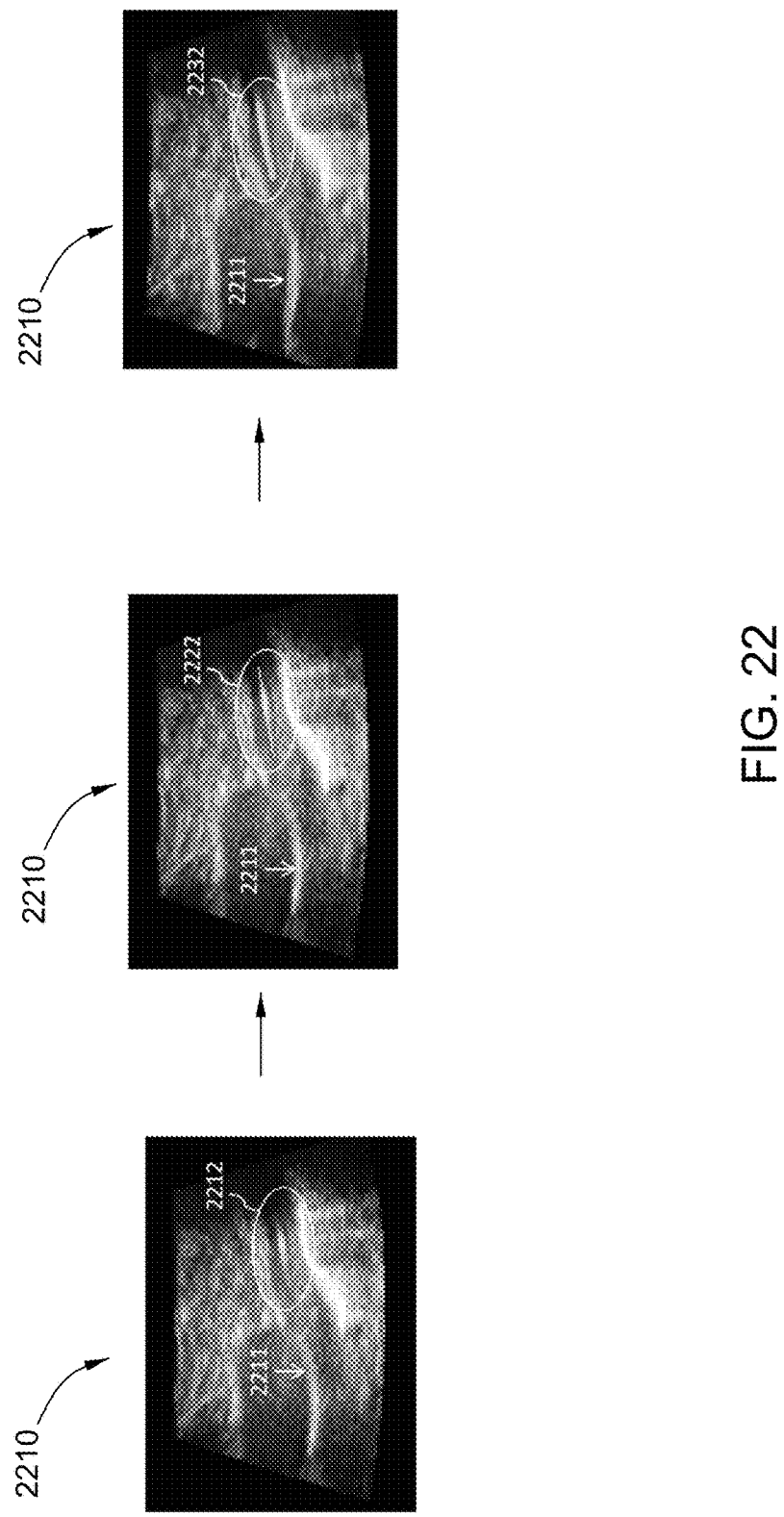
FIG. 22 is a schematic view of an exemplary process of the method of FIG. 21.

Referring to FIGS. 21 and 22, a detailed flowchart of an image compositing method 2100 and a schematic view of an exemplary process performed by the composite image generating module 246 and the image display module 247 are shown, respectively. In one embodiment, the method 2100 includes 2110-2140.

In step 2110, a blood vessel centerline cut image is created performed by the composite image generating module 246. For example, based on the method disclosed in the U.S. patent application Ser. No. 12/645,781, a 3D blood vessel image (not shown) can be obtained. In this 3D blood vessel image, a 2D cut image 2210 along the blood vessel centerline is extracted. In the 2D cut image 2210, a blood vessel 2211 is shown, and may be a part 2212 of the catheter is also shown. Because the catheter may not be located along the blood vessel centerline, the part 2212 may not display the catheter clearly, or there may be no catheter image in the 2D cut image 2210.

In step 2120, a catheter centerline 3D trajectory is projected onto the 2D cut image 2210 performed by the composite image generating module 246. Based on the method 400 mentioned above, a true catheter centerline 3D trajectory is calculated, and then the calculated catheter centerline 3D trajectory can be projected onto the 2D cut image 2210, and generate a projected catheter centerline 2222.

In step 2130, a catheter image on the 2D cut image 2210 is repaired by the composite image generating module 246. Based on the input parameter data of the catheter from the data input unit 230, for example, the diameter of the catheter, a catheter image 2232 is repaired on the 2D cut image 2210 through appropriate algorithms.

In step 2140, the repaired 2D cut image 2210 is then displayed through the monitor 250 by the image display module 247. Then, operators can apply this repaired 2D cut image 2210 to guide them to insert the catheter 2232 into the blood vessel 2211. In some embodiments, the operators also can apply the un-repaired 2D cut image 2210 (the middle image of FIG. 22), and thus, this step 2130 may be omitted accordingly. In other embodiments, the cut image may be cut along the calculated catheter centerline 3D trajectory, and then a catheter image is repaired on this catheter centerline cut image.

In some embodiments, after a catheter and a corresponding blood vessel are detected based on above methods, it is determined whether the detection results of the catheter and the corresponding blood vessel, when compared, satisfy predetermined criterion. The predetermined criterion of the two detection results may include shape matching detection, intensity contrast detection, or other image quality detection. If the detection result of the blood vessel is not satisfied compared with the detection result of the catheter, a ROI of the catheter is extracted, and then the blood vessel is re-detected in the ROI (smaller detection region than original 3D image), which can obtain a better detection result than the original detection result. On the contrary, if the detection result of the catheter is not satisfied compared with the detection result of the blood vessel, a ROI of the blood vessel is extracted, and then the catheter is re-detected in the ROI, which can obtain a better detection result than the original detection result. After the final detection results of the catheter and the blood vessel are determined, a better quality of detection result showing both the catheter and blood vessel can be obtained accordingly, for example, by using the image compositing method 2100.

In an embodiment, before extracting the first ROIs, the original 3D ultrasound image is smoothed by using a smooth algorithm based on the probabilistic speckle model using Fisher-Tippett distribution.

In an embodiment, the generating the first likelihood map, the second likelihood map, and the third likelihood map includes building a 3D catheter template based on an acoustic signature and physical properties of the catheter when viewed under ultrasound, and generating the first likelihood map, the second likelihood map, and the third likelihood map by using the 3D catheter template.

In an embodiment, the 3D catheter template includes three 3D cubical bars Vhole, Vbody, and Vbackground respectively representing a catheter inner hole, a catheter body, and a catheter outside neighboring region.

In an embodiment, the 3D cubical bars $V_{hole}$ and $V_{background}$ are defined as dark feature, and the 3D cubical bars $V_{body}$ is defined as bright feature, a matching result M to generate the candidate catheters from the original 3D ultrasound images is calculated as $M=W_{bright}*S_{body}/\#V_{body}+W_{dark}*(S_{hole}+S_{background})/(\#V_{hole}+\#V_{background})$. S represents the intensity sum of a region, #V represents the pixel number in a region, and W represents a weighting factor.

In an embodiment, determining the integrity of the longest catheter centerline through comparing a plurality of calculated catheter centerline 3D trajectories in the third likelihood map includes repeating the steps of extracting the second ROI, generating the third likelihood map, and updating the longest catheter centerline; and finishing integrity determination based on predetermined conditions.

In an embodiment, finishing integrity determination based on predetermined conditions includes: when the repeating times of the steps is greater than a predetermined value, finishing the integrity determination; or when a detection length on a XY-axis plane of the longest catheter centerline is not increase between two consecutive repeating steps, finishing the integrity determination; or when a difference of two detection lengths on a XY-axis plane or on a ZY-axis plane of the longest catheter centerline in two consecutive repeating steps is greater than a predetermined value, finishing the integrity determination.

In an embodiment, the method further includes repairing the projected catheter centerline based on a predetermined catheter diameter.

In an embodiment, calculating a 3D trajectory of a catheter centerline of the catheter includes generating a plurality of candidate catheters from the original 3D ultrasound image, and pruning false catheters of the plurality of candidate catheters.

In an embodiment, calculating a 3D trajectory of a catheter centerline of the catheter further comprises: refining a true catheter centerline 3D trajectory.

In an embodiment, the method further includes a step between "calculating a 3D trajectory of the blood vessel" and "creating a blood vessel centerline 2D cut image along a blood vessel centerline trajectory based on the calculated 3D trajectory of the blood vessel." The step includes: determining which one of detection results of the catheter and the blood vessel is not satisfied based on predetermined criterion; when the detection result of the blood vessel is not satisfied compared with the detection result of the catheter, re-calculating a 3D trajectory of the blood vessel based on a ROI of the catheter; and when the detection result of the catheter is not satisfied compared with the detection result of the blood vessel, re-calculating a 3D trajectory of a catheter centerline of the catheter based on a ROI of the blood vessel.

While exemplary embodiments of the invention have been described herein, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. An apparatus comprising:
   a 3D ultrasound image acquiring module configured to capture an original 3D ultrasound image; and
   a catheter centerline 3D trajectory generating module configured to detect and to visualize a catheter in the original 3D ultrasound image,
   wherein the catheter centerline 3D trajectory generating module comprises:
      a first likelihood map generating sub-module configured to generate a first likelihood map of catheter location comprising a plurality of candidate catheters therein from the original 3D ultrasound image;
      a catheter plane calculating sub-module configured to calculate XY-axis coordinates of a centerline of each of the plurality of candidate catheters on a projected plane of the first likelihood map; and
      an orthogonal coordinate plane calculating sub-module configured to calculate Z-axis coordinates of the centerline of each of the plurality of candidate catheters on a flattened curved plane of the first likelihood map.

2. The apparatus of claim 1, further comprising:
   a false catheter centerline 3D trajectory pruning module comprising:
      a ROI extracting sub-module configured to extract first ROIs of the candidate catheter centerline 3D trajectories from the original 3D ultrasound image;
      a second likelihood map generating sub-module configured to generate a second likelihood map of catheter location comprising the plurality of candidate catheters therein based on the first ROIs; and
      a projected plane detecting sub-module configured to select a longest catheter centerline of the plurality of candidate catheters on a projected plane of the second likelihood map.

3. The apparatus of claim 2, wherein the false catheter centerline 3D trajectory pruning module further comprises:
   a flattened curved plane detecting sub-module configured to determine whether the longest catheter centerline on a flattened curved plane of the second likelihood map satisfies predetermined catheter shape requirements.

4. The apparatus of claim 3, wherein the catheter shape requirements comprise a ratio between a long axis and a short axis of a determined intensity distribution region on the flattened curved plane of the second likelihood map is greater than a predetermined value.

5. The apparatus of claim 3, further comprising:
   a true catheter centerline 3D trajectory refining module comprising:
      a ROI extracting sub-module configured to extract a second ROI of the longest catheter centerline 3D trajectory from the original 3D ultrasound image;
      a third likelihood map generating sub-module configured to generate a third likelihood map of catheter location comprising the longest catheter therein based on the second ROI; and
      an integrity detecting sub-module configured to determine the integrity of the longest catheter centerline through comparing a plurality of calculated catheter centerline 3D trajectories in the third likelihood map.

6. The apparatus of claim 5, wherein the candidate catheters in the first, second, and third likelihood maps are generated based on a 3D catheter template.

7. The apparatus of claim 6, wherein the 3D catheter template comprises three 3D cubical bars $V_{hole}$, $V_{body}$, and $V_{background}$ respectively representing a catheter inner hole, a catheter body, and a catheter outside neighboring region.

8. The apparatus of claim 7, wherein the 3D cubical bars $V_{hole}$ and $V_{background}$ are defined as dark feature, and the 3D cubical bar $V_{body}$ is defined as bright feature, a matching result M to generate the candidate catheters from the original 3D ultrasound image is calculated as $M = W_{bright} * S_{body} / \#V_{body} + W_{dark} * (S_{hole} + S_{background}) / (\#V_{hole} + \#V_{background})$, where S represents the intensity sum of a region, #V represents the pixel number in a region, and W represents a weighting factor.

9. A method comprising:
   capturing an original 3D ultrasound image;
   generating a first likelihood map of catheter location comprising a plurality of candidate catheters therein from the original 3D ultrasound image;
   detecting a true catheter from the plurality of candidate catheters, and
   displaying the true catheter on a display;
   wherein detecting a true catheter from the plurality of candidate catheters comprises:
      calculating XY-axis coordinates of a centerline of each of the plurality of candidate catheters on a projected plane of the first likelihood map; and
      calculating Z-axis coordinates of the centerline of each of the plurality of candidate catheters on a flattened curved plane of the first likelihood map.

10. The method of claim 9, wherein calculating XY-axis coordinates of a centerline of each of the plurality of candidate catheters on a projected plane of the first likelihood map comprises:
    projecting the catheter centerline of each of the plurality of candidate catheters onto a XY-axis plane of the first likelihood map; and
    calculating coordinates of the projected catheter centerlines.

11. The method of claim 10, wherein calculating Z-axis coordinates of the centerline of each of the plurality of candidate catheters on a flattened curved plane of the first likelihood map comprises:
    flattening a curved surface of each of the plurality of candidate catheters of the first likelihood map which the corresponding catheter centerline is located;
    calculating an intensity distribution region of each of the plurality of candidate catheters on the corresponding flattened curved plane; and
    calculating coordinates of a curve representing depth information of a catheter centerline of each of the plurality of candidate catheters of the first likelihood map based on the calculated intensity distribution regions.

12. The method of claim 11, wherein the coordinates of the projected catheter centerlines and the coordinates of the curves representing depth information of catheter centerlines of the plurality of candidate catheters are calculated based on Hough Transform and polynomial curve fitting algorithms.

13. The method of claim 9, wherein detecting a true catheter from the plurality of candidate catheters further comprises:
    extracting first ROIs of the candidate catheter centerline 3D trajectories from the original 3D ultrasound image;
    generating a second likelihood map of catheter location comprising the plurality of candidate catheters therein based on the first ROIs; and selecting a longest catheter centerline of the plurality of candidate catheters on a projected plane of the second likelihood map.

14. The method of claim 13, wherein detecting a true catheter from the plurality of candidate catheters further comprises:
   determining whether the longest catheter centerline on a flattened curved plane of the second likelihood map satisfies catheter shape requirements.

15. The method of claim 14, wherein the catheter shape requirements comprise a ratio between a long axis and a short axis of a determined intensity distribution region on the flattened curved plane of the second likelihood map is greater than a predetermined value.

16. The method of claim 14, wherein detecting a true catheter from the plurality of candidate catheters further comprises:
   extracting a second ROI of the longest catheter centerline 3D trajectory from the original 3D ultrasound image;
   generating a third likelihood map of catheter location comprising the longest catheter therein based on the second ROI; and
   determining the integrity of the longest catheter centerline through comparing a plurality of calculated catheter centerline 3D trajectories in the third likelihood map.

17. A method, comprising:
   capturing an original 3D ultrasound image;
   calculating a 3D trajectory of a catheter centerline of a catheter;
   calculating a 3D trajectory of a blood vessel;
   creating a blood vessel centerline 2D cut image along a blood vessel centerline trajectory based on the calculated 3D trajectory of the blood vessel; and
   projecting the 3D trajectory of the catheter centerline of the catheter onto the created blood vessel centerline 2D cut image,
   wherein calculating the 3D trajectory of the catheter centerline comprises:
      generating a first likelihood map of catheter locations comprising a plurality of candidate catheters therein from the original 3D ultrasound image;
      calculating XY-axis coordinates of a centerline of each of the plurality of candidate catheters on a projected plane of the first likelihood map; and
      calculating Z-axis coordinates of the centerline of each of the plurality of candidate catheters on a flattened curved plane of the first likelihood map.

18. A method, comprising:
   capturing an original 3D ultrasound image;
   calculating a 3D trajectory of a catheter;
   calculating a 3D trajectory of a blood vessel;
   determining which one of detection results of the catheter and the blood vessel is not satisfied based on predetermined criterion;
   when the detection result of the blood vessel is not satisfied compared with the detection result of the catheter, re-calculating a 3D trajectory of the blood vessel based on a ROI of the catheter;
   when the detection result of the catheter is not satisfied compared with the detection result of the blood vessel, re-calculating a 3D trajectory of a catheter centerline of the catheter based on a ROI of the blood vessel; and
   combining the calculated catheter image and the calculated blood vessel image to become a composite image.

* * * * *